United States Patent
Cui et al.

(10) Patent No.: US 11,771,764 B2
(45) Date of Patent: Oct. 3, 2023

(54) CD47 BLOCKADE WITH RADIATION THERAPY

(71) Applicant: TRILLIUM THERAPEUTICS ULC, Mississauga (CA)

(72) Inventors: Lei Cui, Etobicoke (CA); Lisa Danae Schultz Johnson, Etobicoke (CA)

(73) Assignee: Pfizer Inc., New York, NY (US)

( * ) Notice: Subject to any disclaimer, the term of this patent is extended or adjusted under 35 U.S.C. 154(b) by 285 days.

(21) Appl. No.: 16/759,981

(22) PCT Filed: Nov. 5, 2018

(86) PCT No.: PCT/CA2018/051392
§ 371 (c)(1),
(2) Date: Apr. 28, 2020

(87) PCT Pub. No.: WO2019/084692
PCT Pub. Date: May 9, 2019

(65) Prior Publication Data
US 2021/0244816 A1    Aug. 12, 2021

Related U.S. Application Data

(60) Provisional application No. 62/582,008, filed on Nov. 6, 2017.

(51) Int. Cl.
| | | |
|---|---|---|
| *A61K 41/00* | (2020.01) | |
| *A61K 47/68* | (2017.01) | |
| *A61P 35/00* | (2006.01) | |
| *A61K 38/17* | (2006.01) | |
| *A61N 5/10* | (2006.01) | |
| *C07K 14/705* | (2006.01) | |

(52) U.S. Cl.
CPC ...... *A61K 41/0038* (2013.01); *A61K 38/1774* (2013.01); *A61K 47/68* (2017.08); *A61N 5/1077* (2013.01); *A61P 35/00* (2018.01); *C07K 14/70503* (2013.01); *A61N 2005/1098* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 6,277,375 B1 | 8/2001 | Ward | |
| 6,913,894 B2 | 7/2005 | Buhring et al. | |
| 8,562,997 B2 | 10/2013 | Jaiswal et al. | |
| 9,969,789 B2 | 5/2018 | Uger et al. | |
| 9,979,789 B2 | 5/2018 | Lu et al. | |
| 10,906,954 B2* | 2/2021 | Uger ............... | C07K 14/70503 |
| 2011/0135641 A1 | 6/2011 | Isenberg et al. | |
| 2011/0237498 A1 | 9/2011 | Raymond et al. | |
| 2012/0189625 A1 | 7/2012 | Wang et al. | |
| 2015/0329616 A1 | 11/2015 | Uger et al. | |
| 2018/0312563 A1 | 11/2018 | Uger et al. | |
| 2019/0091290 A1 | 3/2019 | Lin et al. | |
| 2019/0093174 A1 | 3/2019 | Wang et al. | |
| 2019/0255082 A1 | 8/2019 | Linderoth et al. | |
| 2019/0269756 A1 | 9/2019 | Linderoth et al. | |
| 2020/0157179 A1 | 5/2020 | Lin et al. | |
| 2021/0206829 A1* | 7/2021 | Uger ...................... | A61P 35/02 |

FOREIGN PATENT DOCUMENTS

| | | |
|---|---|---|
| WO | WO-2010/017332 A2 | 2/2010 |
| WO | WO-2010/070047 A1 | 6/2010 |
| WO | WO-2010/083253 A2 | 7/2010 |
| WO | WO-2012/170250 A1 | 12/2012 |
| WO | WO-2013/056352 A1 | 4/2013 |
| WO | WO-2013/109752 A1 | 7/2013 |
| WO | WO-2014/093678 A2 | 6/2014 |
| WO | WO-2014/094122 A1 | 6/2014 |
| WO | WO-2014/123580 A1 | 8/2014 |
| WO | WO-2015/103989 A1 | 7/2015 |
| WO | WO-2016/004875 A1 | 1/2016 |
| WO | WO-2016/022971 A1 | 2/2016 |
| WO | WO-2017/177333 A1 | 10/2017 |
| WO | WO-2017/180519 A1 | 10/2017 |
| WO | WO-2018/176132 A1 | 10/2018 |
| WO | WO-2018/236904 | 12/2018 |
| WO | WO-2019/084692 A1 | 5/2019 |

OTHER PUBLICATIONS

Wang et al. (Mol. Therapy Oct. 2013 21(10): 1919-1929) (Year: 2013).*
Demaria and Formenti (Frontiers in Oncology Oct. 26, 2012 vol. 2: Article 153, pp. 1-7) (Year: 2012).*
Cui et al., (J. for Immunotherapy of Cancer, Society for Immunotherapy of Cancer; Nov. 10-12, 2017;NationalHarbor,MD, published Nov. 7, 2017) (Year: 2017).*
Extended European Search Report issued by the European Patent Office in regards to EPO Application No. 18874304.1, dated Jul. 29, 2021.
Isenberg et al., Thrombospondin-1 and CD47 limit cell and tissue survival of radiation injury, *Am. J. Path.* 173:1100-1112 (2008).
Cui et al., The anti-tumor effect of radiation therapy is enhanced with the addition of TTI-621 (SIRPαFc), an immune checkpoint inhibitor blocking the CD47 "do not eat" signal, presented by Trillium Therapeutics Inc., Mississauga, Ontario, Canada (Abstract) at Society for Immunotherapy of Cancer; Nov. 10-12, 2017; National Harbor, MD (Nov. 2017).

(Continued)

*Primary Examiner* — Peter J Reddig
(74) *Attorney, Agent, or Firm* — Stephen E. Moyer

(57) ABSTRACT

This patent application relates to the treatment of cancer and other diseases that have a CD47+ phenotype. Treatment involves the use of radiation and a CD47-binding agent, preferably a CD47-binding form of human signal regulatory protein alpha (SIRPa) that inhibits activation of the CD47/SIRPa axis and mediates phagocytosis of CD47+ disease cells. An anti-cancer effect of a CD47 blocking agent is enhanced when combined with radiation therapy. The anti-cancer effect of a CD47 blocking agent such as SIRPaFc is enhanced when combined with radiation therapy.

18 Claims, 14 Drawing Sheets

Figure 1:
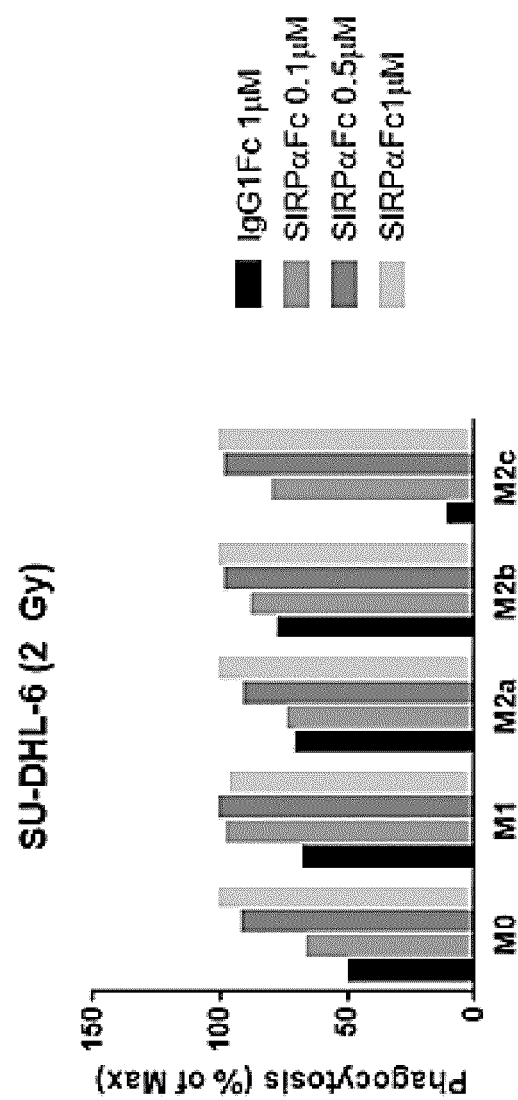

Specification includes a Sequence Listing.

(56) References Cited

OTHER PUBLICATIONS

Cui et al., The Anti-tumor Effect of Radiation Therapy is Enhanced with the Addition of TTI-621 (SIRPαFc), an Immune Checkpoint Inhibitor Blocking the CD47 "Do Not Eat" Signal. Poster presented at the Society for Immunotherapy of Cancer Annual Meeting: Nov. 8-12, 2017; National Harbor, MD.
GenBank Accession No. CAA71403.1, SIRP-alpha1 [*Homo sapiens*], dated May 14, 1997.
GenBank Accession No. BAC04226.1, unnamed protein product [*Homo sapiens*], Jan. 9, 2008.
GenBank Accession No. BAC05014.1, unnamed protein product [*Homo sapiens*], Jan. 9, 2008.
GenBank Accession No. BAC05016.1, unnamed protein product [*Homo sapiens*], Jan. 9, 2008.
GenBank Accession No. BAC85350.1, unnamed protein product [*Homo sapiens*], Sep. 14, 2006.
GenBank Accession No. BAC85429.1, unnamed protein product [*Homo sapiens*], Sep. 14, 2006.
GenBank Accession No. BAC85529.1, unnamed protein product [*Homo sapiens*], Jan. 9, 2008.
GenBank Accession No. BAG65283.1, unnamed protein product [*Homo sapiens*], Jul. 24, 2008.
GenBank Accession No. CAC20454.1, immunoglobulin heavy chain constant region gamma 1, partial [*Homo sapiens*], Jul. 14, 2016.
GenBank Accession No. CAC20457.1, immunoglobulin heavy chain constant region gamma 4, partial [*Homo sapiens*], Jul. 14, 2016.
International Preliminary Report on Patentability, PCT/CA2018/051392, dated May 12, 2020.
International Search Report and Written Opinion, PCT/CA2018/051392, dated Jan. 16, 2019.
Maxhimer et al., Radioprotection in normal tissue and delayed tumor growth by blockade of CD47 signaling, *Sci. Transl. Med.* 1(3):3ra7 (2009).
Nayerossadat et al., Viral and nonviral delivery systems for gene delivery, *Adv. Biomed. Res.* 1:27 (2012).
NCBI Accession No. NP_542970.1, tyrosine-protein phosphatase non-receptor type substrate 1 isoform 1 precursor [*Homo sapiens*], dated Sep. 20, 2020.
Soto-Pantoja et al., Therapeutic opportunities for targeting the ubiquitous cell surface receptor CD47, *Expert Opin. Ther. Targets.* 17(1):89-103 (2013).
UniProtKB/Swiss-Prot: P01857, Immunoglobulin heavy constant gamma 1, Aug. 12, 2020.
UniProtKB/Swiss-Prot: P01859, Immunoglobulin heavy constant gamma 2, Aug. 12, 2020.
UniProtKB/Swiss-Prot: P01860, Immunoglobulin heavy constant gamma 3, Aug. 12, 2020.
UniProtKB/Swiss-Prot: P01861, Immunoglobulin heavy constant gamma 4, Aug. 12, 2020.
Willingham et al., The CD-47-signal regulatory protein alpha (SIRPa) interaction is a therapeutic target for human solid tumors, *PNAS*, 109(17):6662-7 (2012).

\* cited by examiner

Figure 2B
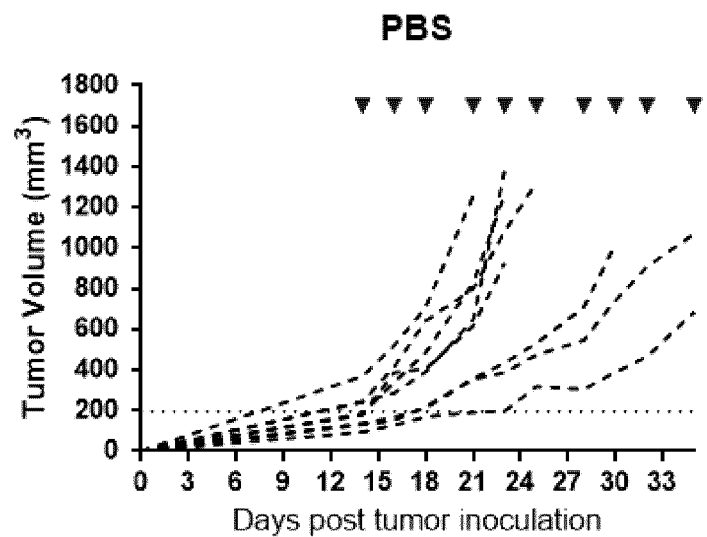
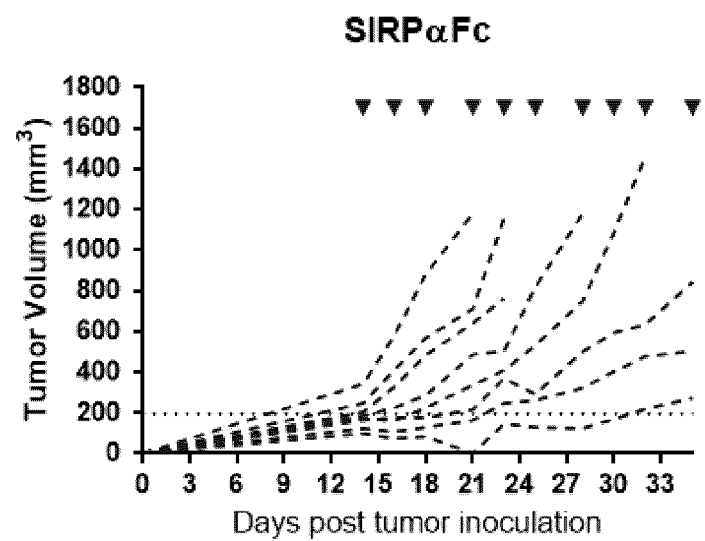
Figure 2C

Figure 2G
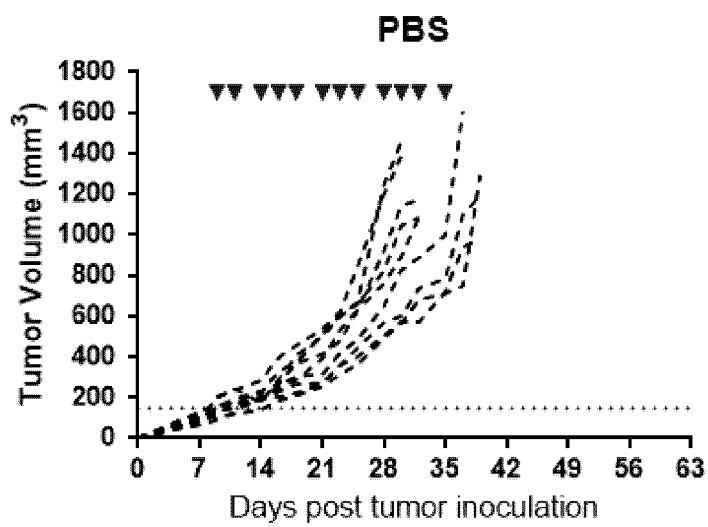
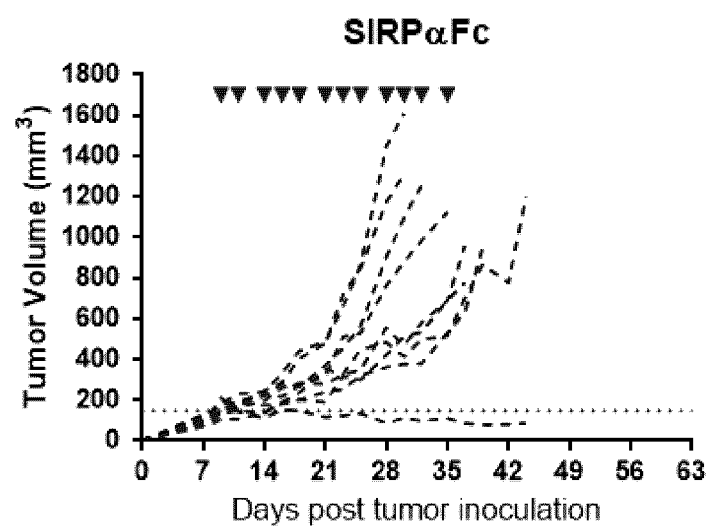
Figure 2H

Figure 2I
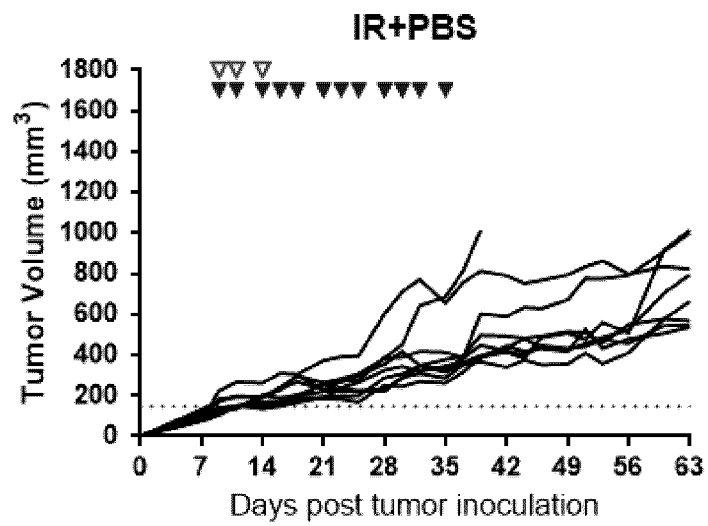
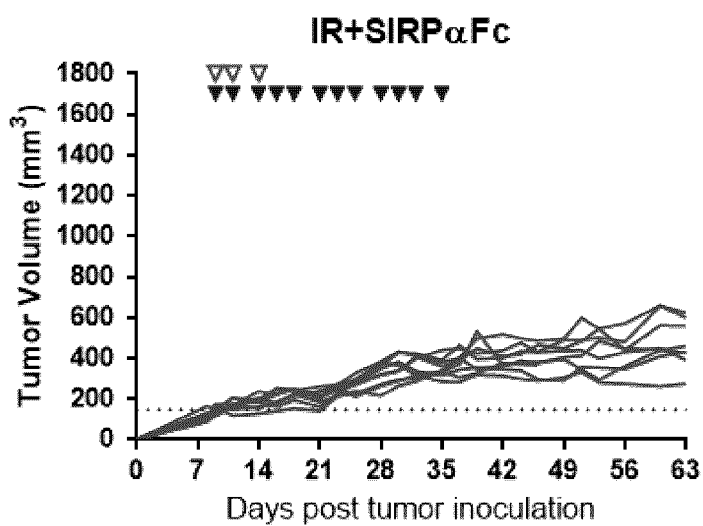
Figure 2J

Figure 4A:
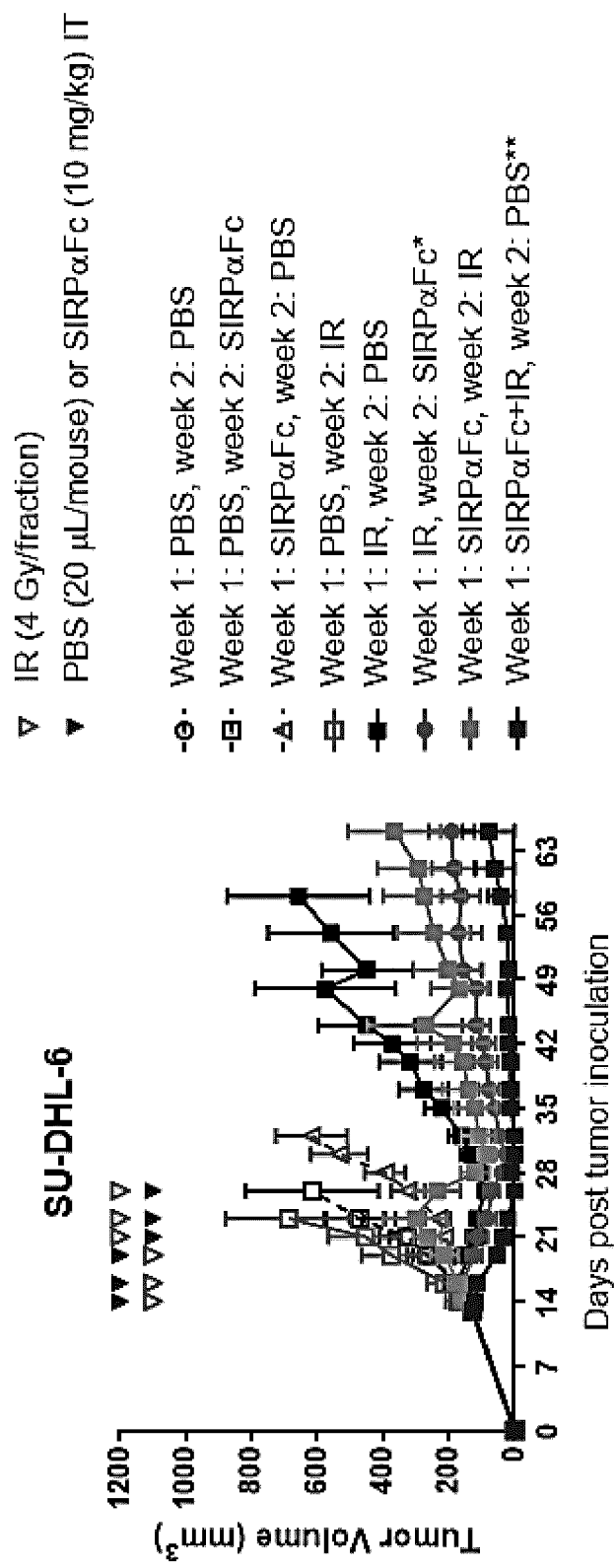
Figure 4D:
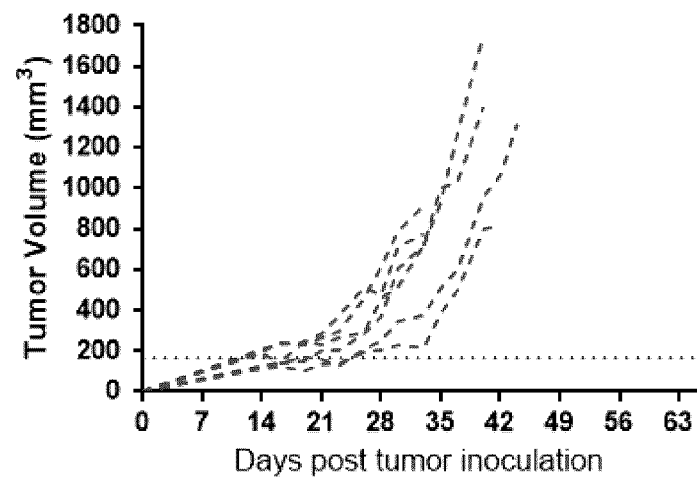
Figure 4E:
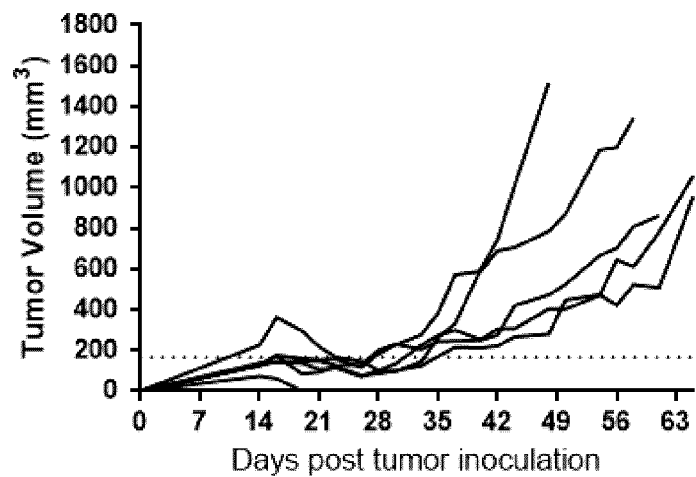

Figure 4B
Week 1: PBS, week 2: PBS
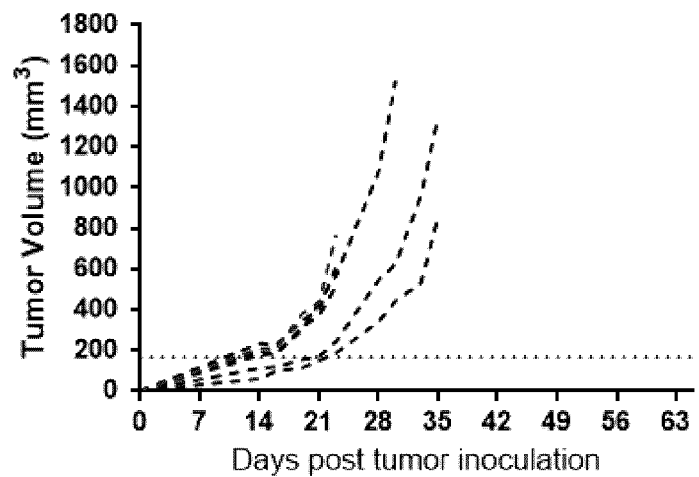
Week 1: PBS, week 2: SIRPαFc
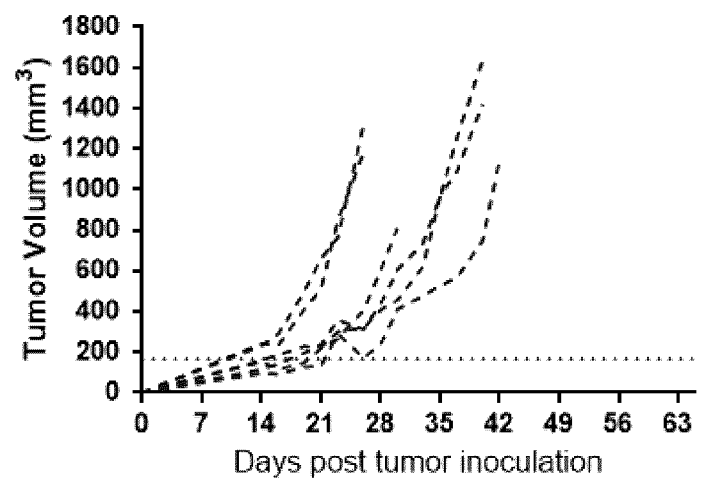
Figure 4C Figure 4F
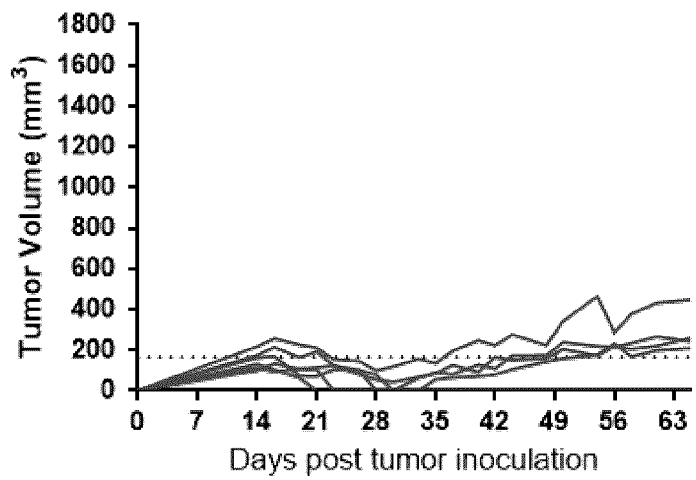
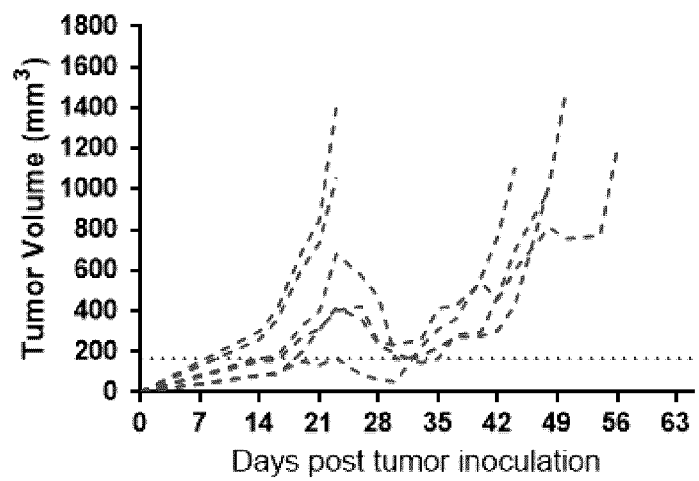
Figure 4G Figure 4H
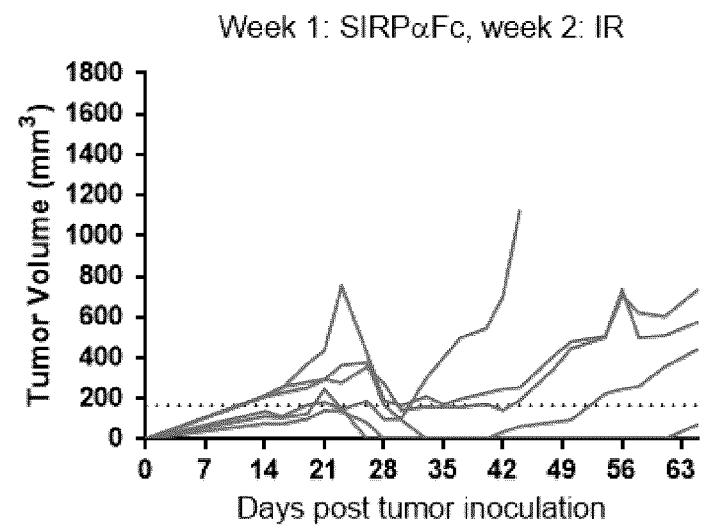
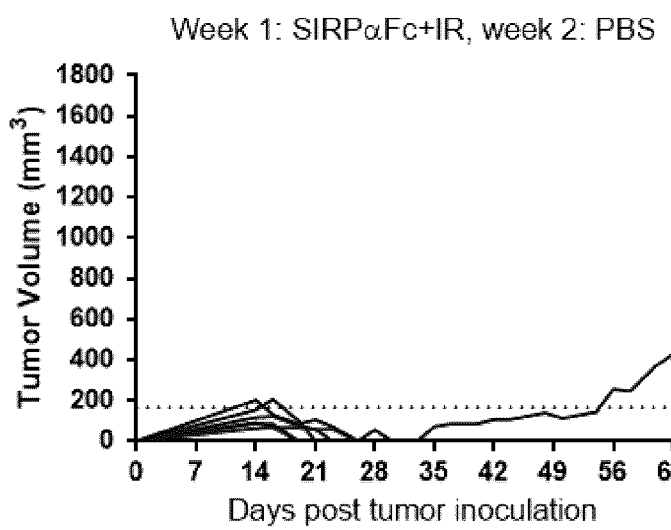
Figure 4I

SEQUENCE LISTING

```
<160> NUMBER OF SEQ ID NOS: 15

<210> SEQ ID NO 1
<211> LENGTH: 106
<212> TYPE: PRT
<213> ORGANISM: Homo sapiens

<400> SEQUENCE: 1

Glu Glu Leu Gln Val Ile Gln Pro Asp Lys Ser Val Ser Val Ala Ala
1               5                   10                  15

Gly Glu Ser Ala Ile Leu His Cys Thr Val Thr Ser Leu Ile Pro Val
            20                  25                  30

Gly Pro Ile Gln Trp Phe Arg Gly Ala Gly Pro Ala Arg Glu Leu Ile
        35                  40                  45

Tyr Asn Gln Lys Glu Gly His Phe Pro Arg Val Thr Thr Val Ser Glu
    50                  55                  60

Ser Thr Lys Arg Glu Asn Met Asp Phe Ser Ile Ser Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Thr Glu Phe Lys Ser Gly Ala
            100                 105

<210> SEQ ID NO 2
<211> LENGTH: 118
<212> TYPE: PRT
<213> ORGANISM: Homo sapiens

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 3
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
```

-continued

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser His
            20                  25                  30

Glu Asp Pro Glu Val Lys Phe Asn Trp Tyr Val Asp Gly Val Glu Val
        35                  40                  45

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 4
<211> LENGTH: 216
<212> TYPE: PRT
<213> ORGANISM: Homo sapiens

<400> SEQUENCE: 4

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Asn Ser Thr Phe Arg Val Val Ser Val Leu Thr Val Val His Gln
65                  70                  75                  80

Asp Trp Leu Asn Gly Lys Glu Tyr Lys Cys Lys Val Ser Asn Lys Gly
                85                  90                  95

Leu Pro Ala Pro Ile Glu Lys Thr Ile Ser Lys Thr Lys Gly Gln Pro
            100                 105                 110

Arg Glu Pro Gln Val Tyr Thr Leu Pro Pro Ser Arg Glu Glu Met Thr
        115                 120                 125

Lys Asn Gln Val Ser Leu Thr Cys Leu Val Lys Gly Phe Tyr Pro Ser
130                 135                 140

```
Asp Ile Ser Val Glu Trp Glu Ser Asn Gly Gln Pro Glu Asn Asn Tyr
145                 150                 155                 160

Lys Thr Thr Pro Pro Met Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 5
<211> LENGTH: 217
<212> TYPE: PRT
<213> ORGANISM: Homo sapiens

<400> SEQUENCE: 5

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Lys Trp Tyr
        35                  40                  45

Val Asp Gly Val Glu Val His Asn Ala Lys Thr Lys Pro Arg Glu Glu
    50                  55                  60

Gln Tyr Asn Ser Thr Phe Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Ser Gly Gln Pro Glu Asn Asn
145                 150                 155                 160

Tyr Asn Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Ile
            180                 185                 190

Phe Ser Cys Ser Val Met His Glu Ala Leu His Asn Arg Phe Thr Gln
        195                 200                 205

Lys Ser Leu Ser Leu Ser Pro Gly Lys
    210                 215

<210> SEQ ID NO 6
<211> LENGTH: 229
<212> TYPE: PRT
<213> ORGANISM: Homo sapiens

<400> SEQUENCE: 6

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30
```

Leu Met Ile Ser Arg Thr Pro Glu Val Thr Cys Val Val Asp Val
            35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 7
<211> LENGTH: 229
<212> TYPE: PRT
<213> ORGANISM: Homo sapiens

<400> SEQUENCE: 7

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

```
Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
210                 215                 220

Leu Ser Leu Gly Lys
225

<210> SEQ ID NO 8
<211> LENGTH: 344
<212> TYPE: PRT
<213> ORGANISM: Homo sapiens

<400> SEQUENCE: 8

Glu Glu Leu Gln Val Ile Gln Pro Asp Lys Ser Val Ser Val Ala Ala
1               5                   10                  15

Gly Glu Ser Ala Ile Leu His Cys Thr Val Thr Ser Leu Ile Pro Val
            20                  25                  30

Gly Pro Ile Gln Trp Phe Arg Gly Ala Gly Pro Ala Arg Glu Leu Ile
        35                  40                  45

Tyr Asn Gln Lys Glu Gly His Phe Pro Arg Val Thr Thr Val Ser Glu
50                  55                  60

Ser Thr Lys Arg Glu Asn Met Asp Phe Ser Ile Ser Ile Ser Asn Ile
65                  70                  75                  80

Thr Pro Ala Asp Ala Gly Thr Tyr Tyr Cys Val Lys Phe Arg Lys Gly
                85                  90                  95

Ser Pro Asp Thr Glu Phe Lys Ser Gly Ala Gly Thr Glu Leu Ser Val
            100                 105                 110

Arg Ala Lys Pro Ser Asp Lys Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Pro Ile Glu Lys Thr Ile Ser Lys Ala Lys Gly Gln Pro
225                 230                 235                 240

Arg Glu Pro Gln Val Tyr Thr Leu Pro Pro Ser Arg Asp Glu Leu Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
```

```
                305                 310                 315                 320
Ser Cys Ser Val Met His Glu Ala Leu His Asn His Tyr Thr Gln Lys
                    325                 330                 335

Ser Leu Ser Leu Ser Pro Gly Lys
                340

<210> SEQ ID NO 9
<211> LENGTH: 345
<212> TYPE: PRT
<213> ORGANISM: Homo sapiens

<400> SEQUENCE: 9

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
                20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
        50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Asp Lys Thr His Thr Cys Pro Pro Cys Pro
        115                 120                 125

Ala Pro Glu Leu Leu Gly Gly Pro Ser Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser His Glu Asp Pro Glu Val Lys Phe Asn Trp Tyr
                165                 170                 175

Val Asp Gly Val Glu Val His Asn Ala Lys Thr Lys Pro Arg Glu Glu
            180                 185                 190

Gln Tyr Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Ala Leu Pro Ala Pro Ile Glu Lys Thr Ile Ser Lys Ala Lys Gly Gln
225                 230                 235                 240

Pro Arg Glu Pro Gln Val Tyr Thr Leu Pro Pro Ser Arg Asp Glu Leu
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
        275                 280                 285

Tyr Lys Thr Thr Pro Pro Val Leu Asp Ser Asp Gly Ser Phe Phe Leu
    290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335
```

```
Lys Ser Leu Ser Leu Ser Pro Gly Lys
        340             345

<210> SEQ ID NO 10
<211> LENGTH: 347
<212> TYPE: PRT
<213> ORGANISM: Homo sapiens

<400> SEQUENCE: 10

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
        115                 120                 125

Cys Pro Ala Pro Glu Phe Leu Gly Gly Pro Ser Val Phe Leu Phe Pro
    130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
            180                 185                 190

Glu Glu Gln Phe Asn Ser Thr Tyr Arg Val Val Ser Val Leu Thr Val
        195                 200                 205

Leu His Gln Asp Trp Leu Asn Gly Lys Glu Tyr Lys Cys Lys Val Ser
    210                 215                 220

Asn Lys Gly Leu Pro Ser Ser Ile Glu Lys Thr Ile Ser Lys Ala Lys
225                 230                 235                 240

Gly Gln Pro Arg Glu Pro Gln Val Tyr Thr Leu Pro Pro Ser Gln Glu
                245                 250                 255

Glu Met Thr Lys Asn Gln Val Ser Leu Thr Cys Leu Val Lys Gly Phe
            260                 265                 270

Tyr Pro Ser Asp Ile Ala Val Glu Trp Glu Ser Asn Gly Gln Pro Glu
        275                 280                 285

Asn Asn Tyr Lys Thr Thr Pro Pro Val Leu Asp Ser Asp Gly Ser Phe
    290                 295                 300

Phe Leu Tyr Ser Arg Leu Thr Val Asp Lys Ser Arg Trp Gln Glu Gly
305                 310                 315                 320

Asn Val Phe Ser Cys Ser Val Met His Glu Ala Leu His Asn His Tyr
                325                 330                 335

Thr Gln Lys Ser Leu Ser Leu Ser Leu Gly Lys
            340                 345

<210> SEQ ID NO 11
```

```
<211> LENGTH: 117
<212> TYPE: PRT
<213> ORGANISM: Homo sapiens

<400> SEQUENCE: 11

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro
        115

<210> SEQ ID NO 12
<211> LENGTH: 346
<212> TYPE: PRT
<213> ORGANISM: Homo sapiens

<400> SEQUENCE: 12

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
        115                 120                 125

Cys Pro Ala Pro Val Ala Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp
                165                 170                 175

Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
        195                 200                 205

His Gln Asp Trp Leu Asn Gly Lys Glu Tyr Lys Cys Lys Val Ser Asn
    210                 215                 220
```

```
Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
            245                 250                 255

Met Thr Lys Asn Gln Val Ser Leu Thr Cys Leu Val Lys Gly Phe Tyr
        260                 265                 270

Pro Ser Asp Ile Ala Val Glu Trp Glu Ser Asn Gly Gln Pro Glu Asn
    275                 280                 285

Asn Tyr Lys Thr Thr Pro Pro Val Leu Asp Ser Asp Gly Ser Phe Phe
290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Leu Gly Lys
            340                 345

<210> SEQ ID NO 13
<211> LENGTH: 11
<212> TYPE: PRT
<213> ORGANISM: Artificial Sequence
<220> FEATURE:
<223> OTHER INFORMATION: Synthetic Linker

<400> SEQUENCE: 13

Gly Thr Glu Leu Ser Val Arg Ala Lys Pro Ser
1               5                   10

<210> SEQ ID NO 14
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 14

Gly Gly Gly Gly Ser
1               5

<210> SEQ ID NO 15
<211> LENGTH: 118
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (4)..(4)
<223> OTHER INFORMATION: Sub Val or Ile
<220> FEATURE:
<221> NAME/KEY: MISC_FEATURE
<222> LOCATION: (6)..(6)
<223> OTHER INFORMATION: Sub Ile or Leu
<220> FEATURE:
<221> NAME/KEY: MISC_FEATURE
<222> LOCATION: (21)..(21)
<223> OTHER INFORMATION: Sub Val
<220> FEATURE:
<221> NAME/KEY: MISC_FEATURE
<222> LOCATION: (27)..(27)
<223> OTHER INFORMATION: Sub Ile or Leu
<220> FEATURE:
<221> NAME/KEY: MISC_FEATURE
<222> LOCATION: (31)..(31)
<223> OTHER INFORMATION: Sub Thr, Ser or Phe
<220> FEATURE:
```

```
<221> NAME/KEY: MISC_FEATURE
<222> LOCATION: (47)..(47)
<223> OTHER INFORMATION: Sub Val or Leu
<220> FEATURE:
<221> NAME/KEY: MISC_FEATURE
<222> LOCATION: (53)..(53)
<223> OTHER INFORMATION: Sub Arg
<220> FEATURE:
<221> NAME/KEY: MISC_FEATURE
<222> LOCATION: (54)..(54)
<223> OTHER INFORMATION: Sub Gln
<220> FEATURE:
<221> NAME/KEY: MISC_FEATURE
<222> LOCATION: (56)..(56)
<223> OTHER INFORMATION: Sub Pro or Arg
<220> FEATURE:
<221> NAME/KEY: MISC_FEATURE
<222> LOCATION: (63)..(63)
<223> OTHER INFORMATION: Sub Ile
<220> FEATURE:
<221> NAME/KEY: MISC_FEATURE
<222> LOCATION: (66)..(66)
<223> OTHER INFORMATION: Sub Thr or Gly
<220> FEATURE:
<221> NAME/KEY: MISC_FEATURE
<222> LOCATION: (68)..(68)
<223> OTHER INFORMATION: Sub Arg
<220> FEATURE:
<221> NAME/KEY: MISC_FEATURE
<222> LOCATION: (92)..(92)
<223> OTHER INFORMATION: Sub Ile
<220> FEATURE:
<221> NAME/KEY: MISC_FEATURE
<222> LOCATION: (94)..(94)
<223> OTHER INFORMATION: Sub Val or Leu
<220> FEATURE:
<221> NAME/KEY: MISC_FEATURE
<222> LOCATION: (103)..(103)
<223> OTHER INFORMATION: Sub Val

<400> SEQUENCE: 15

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115
```

CD47 BLOCKADE WITH RADIATION THERAPY

CROSS-REFERENCE TO RELATED APPLICATIONS

This application is a U.S. National Phase of International Application No. PCT/CA2018/0051392 filed Nov. 5, 2018, which claims the benefit under 35 USC § 119 of U.S. Provisional Application No. 62/582,008, filed Nov. 6, 2017.

FIELD

This disclosure relates to the treatment of cancer and other disease cells that have a CD47+ phenotype. Treatment involves the use of radiation and a CD47-binding form of human signal regulatory protein alpha (SIRPα) that inhibits activation of the CD47/SIRPα axis and mediates phagocytosis of the CD47+ disease cells.

INCORPORATION BY REFERENCE OF MATERIALS SUBMITTED ELECTRONICALLY

This application contains, as a separate part of the disclosure, a Sequence Listing in computer readable form (Filename: 53637A_Seqlisting.txt; Size: 27,859 bytes; Created: Apr. 28, 2019), which is incorporated herein by reference in its entirety.

BACKGROUND

CD47 is an immune checkpoint that binds to signal regulatory protein alpha (SIRPα) and delivers a "do not eat" signal to suppress macrophage phagocytosis. Tumor cells frequently overexpress CD47 to evade macrophage-mediated destruction. Trillium's WO2014/094122 describes a protein drug that inhibits the interaction between CD47 and SIRPα. This CD47 blocking agent is a form of human SIRPα that incorporates a particular region of its extracellular domain linked with a particularly useful form of an IgG1-based Fc region. A related form of SIRPα having an IgG4-based Fc region is also described. In these forms, SIRPαFc shows dramatic effects on the viability of cancer cells that present with a CD47+ phenotype. The effect is seen particularly on acute myelogenous leukemia (AML) cells, and on many other types of cancer. A soluble form of SIRP having significantly altered primary structure and enhanced CD47 binding affinity is described in WO2013/109752.

Other CD47 blockade drugs have been described in the literature and these include various CD47 antibodies (see for instance Stanford's U.S. Pat. No. 8,562,997, and InhibRx' WO2014/123580), each comprising different antigen binding sites but having, in common, the ability to compete with endogenous SIRPα for binding to CD47, thereby to allow interaction with macrophages and, ultimately, to increase the rate of CD47+ cancer cell depletion. These CD47 antibodies have activities in vivo that are quite different from those intrinsic to SIRPα-based drugs. The latter, for instance, display negligible binding to red blood cells whereas the opposite property in CD47 antibodies creates a need for strategies that accommodate the drug "sink" that follows administration.

Still other agents are proposed for use in blocking the CD47/SIRPα axis. These include CD47Fc proteins (see Viral Logic's WO2010/083253), and SIRPα antibodies as described in UHN's WO2013/056352, Stanford's WO2016/022971, Eberhard's U.S. Pat. No. 6,913,894, and elsewhere.

The CD47 blockade approach in anti-cancer drug development shows great promise. It would be useful to provide methods and means for improving the effect of these drugs, and in particular for improving the effect of the CD47 blockade drugs, especially those that incorporate SIRPα.

SUMMARY

It has been determined that the anti-cancer benefit of radiation therapy is enhanced when combined with an inhibitor of the SIRPα/CD47 axis, and particularly when such treatment uses a combination of radiation therapy and a CD47 blocking agent that is or comprises a CD47-binding form of SIRPα. This combination therapy is useful to control the vitality, growth and/or proliferation of CD47+ disease cells, such as CD47+ cancer cells that include solid cancers such as ovarian cancers and lung cancers, and blood cancers such as leukemias, lymphomas, myelomas, and the like. The two treatment modalities cooperate in their effects on cancer cells, and can result in the depletion of more cancer cells than can be accounted for by their individual effects.

In one aspect, there is provided a method for treating CD47+ disease cells in a subject in need thereof, comprising administering to the subject, in a treatment effective combination, (1) radiation therapy, and (2) a CD47 blocking agent that comprises a CD47-binding form of human SIRPα. Optionally, the subject is human.

In embodiments, concurrent administration is preferred. In the alternative, CD47 blocking agent is administered to a subject that has received radiation therapy, or a subject that will receive radiation therapy. In consecutive treatment, the effect of one therapy desirably overlaps, within the subject, with the effect of the other therapy.

In other embodiments, the radiation therapy is provided as external beam radiation. In other embodiments, the CD47 blocking agent is or comprises an Fc fusion of a CD47-binding form of SIRPα. In specific embodiments, the Fc fusion can be an IgG1 fusion, an IgG4 fusion, or an IgG fusion that is altered to reduce or eliminate effector function.

In other aspects, there is provided the use of radiation therapy in combination with a CD47 blocking agent that is or comprises a CD47-binding form of SIRPα, for the treatment of a subject presenting with a disease comprising CD47+ disease cells.

In another aspect there is provided an article of manufacture comprising a container comprising a CD47-binding form of SIRPα in an amount suitable for dosing a subject undergoing CD47+ disease therapy, wherein the article or the container comprises instruction to use said SIRPα in combination with radiation therapy.

Many of the CD47 blockade drugs described herein are polypeptides. Another aspect of this disclosure relates to use of a polynucleotide (nucleic acid) that comprises a nucleotide sequence encoding the CD47 blockade drug (and/or a vector and/or a host cell comprising such polynucleotide) to effectively deliver the CD47 blockade drug to the subject. Exemplary nucleic acids include DNA and RNA. Relatedly, the invention includes synthetic genes that comprise said coding sequences and one or more expression control sequences, such as promoters, start codons, or polyadenylation signal sequences. The invention also includes vectors that comprise the nucleic acids or synthetic genes, and isolated cells transformed or transfected with the genes or vectors. The disclosure contemplates use of any of the foregoing (including compositions comprising the foregoing) as part of a combination therapy with radiation therapy.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

REFERENCE TO THE DRAWINGS

FIG. 1:
VPD450 labelled SU-DHL-6 were irradiated with 2 Gy and co-cultured with normal donor derived polarized macrophages: M0 (no priming), M1 (IFN-γ), M2a (IL-4), M2b (HAGG+IL-1β), and M2C (IL-10+TGFβ) in the presence of isotype control human IgG1Fc or SIRPαFc (SEQ #25). Phagocytosis is reported as the percent of maximum phagocytosis for each macrophage subtype.

Figure 2A:
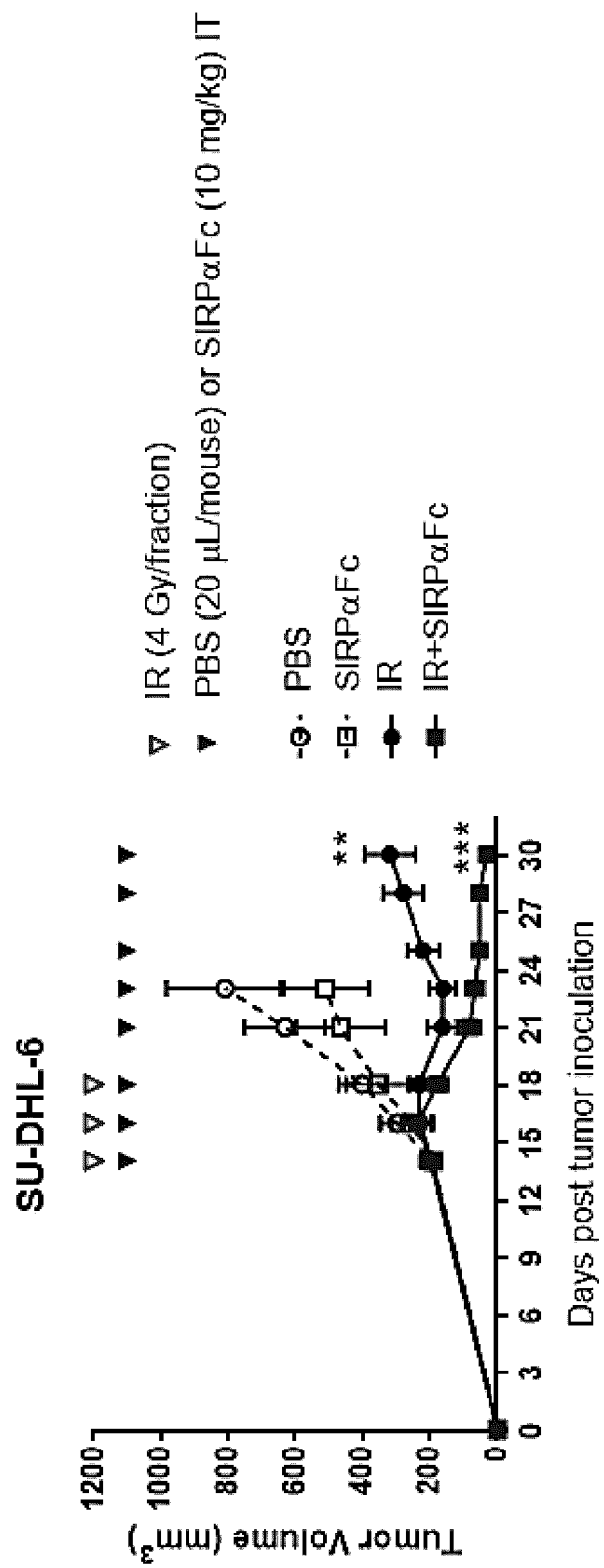
Figure 2D:
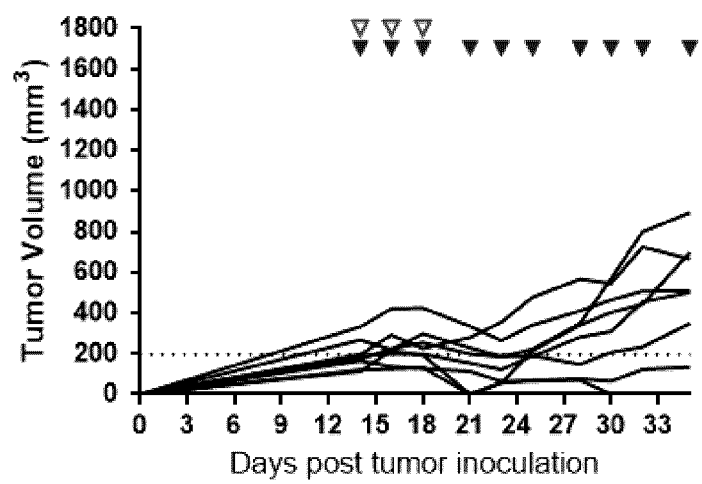
Figure 2E:
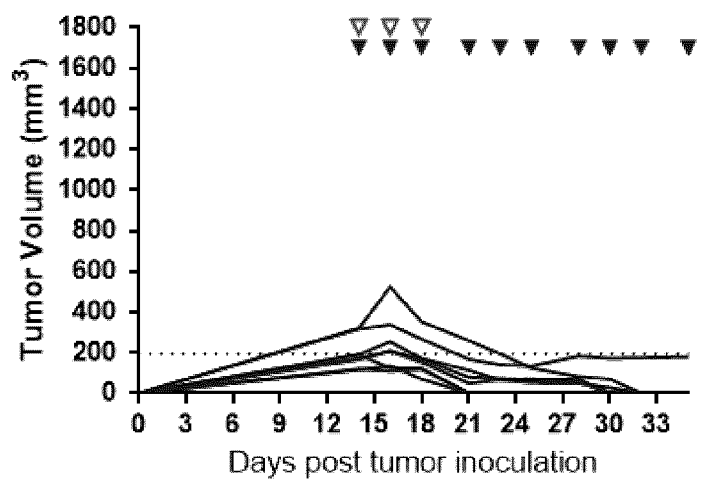
Figure 2F:
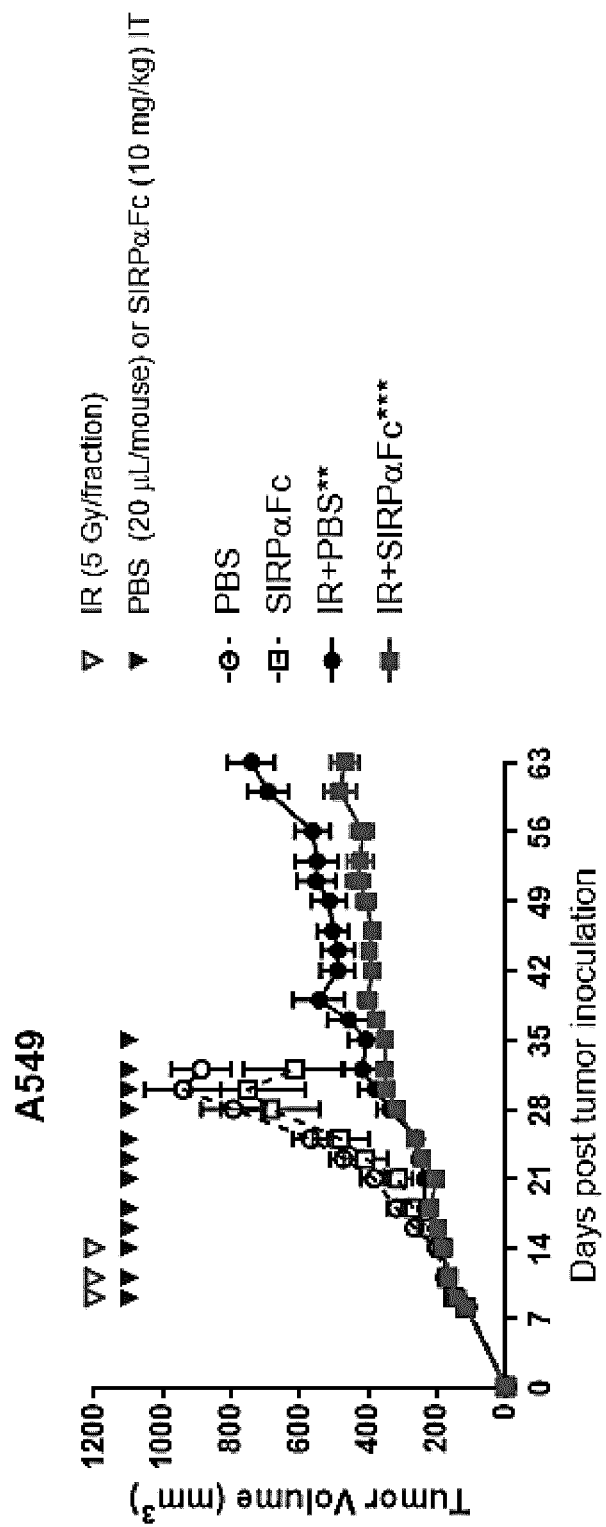

FIGS. 2A-2J:
NOD/SCID mice were implanted subcutaneously with SU-DHL-6 (human B lymphoma) or A549 (human lung carcinoma) cells and treated with intratumoural SIRPαFc, localized irradiation (IR, 225 kVp, 13 mA) to the tumor sites, or IR+SIRPαFc. Mean tumor growth is shown in FIG. 2A and spider plots are shown in FIGS. 2B-2E (for an SU-DHL-6 model). Mean tumor growth is shown in FIG. 2F and spider plots are shown in FIGS. 2G-2J (for an A549 model). P values are in comparison to the PBS control groups (, p<0.01, * p<0.001). No toxicity was observed for all treatment groups as measured by body weight change.

Figure 3:
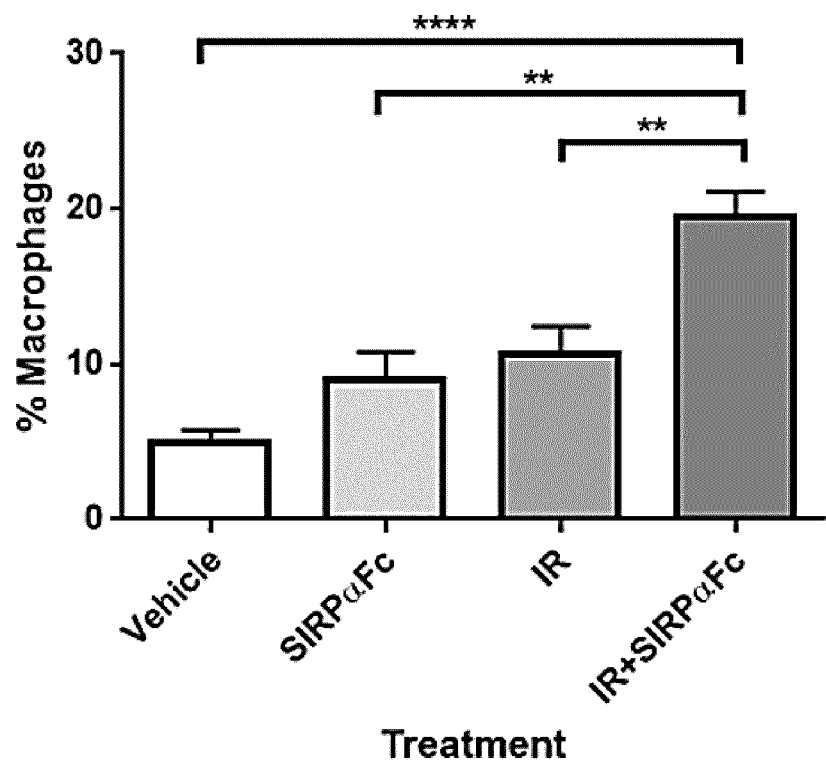

FIG. 3:
The percent of macrophages of total number of cells at the tumor sites following treatment in the SU-DHL-6 model, measured by immunohistochemistry (IHC). Tumor tissues were collected when the animals reached their ethical endpoint (a tumor size exceeding 1.5 cm in any dimension) or on day 33 as shown in FIGS. 2B-2E.

FIGS. 4A-4I:
NOD/SCID mice with palpable SU-DHL-6 tumors were treated with IR and SIRPαFc in a sequential manner or concurrent administration.
(FIG. 4A) Mean growth of SU-DHL-6 tumors in 8 treatment groups.
(FIGS. 4B-4I) Tumor growth spider plots of individual animals. P values are in comparison to the week 1 IR week 2 PBS group (*, p<0.05, **, p<0.01)

Figure 5A:
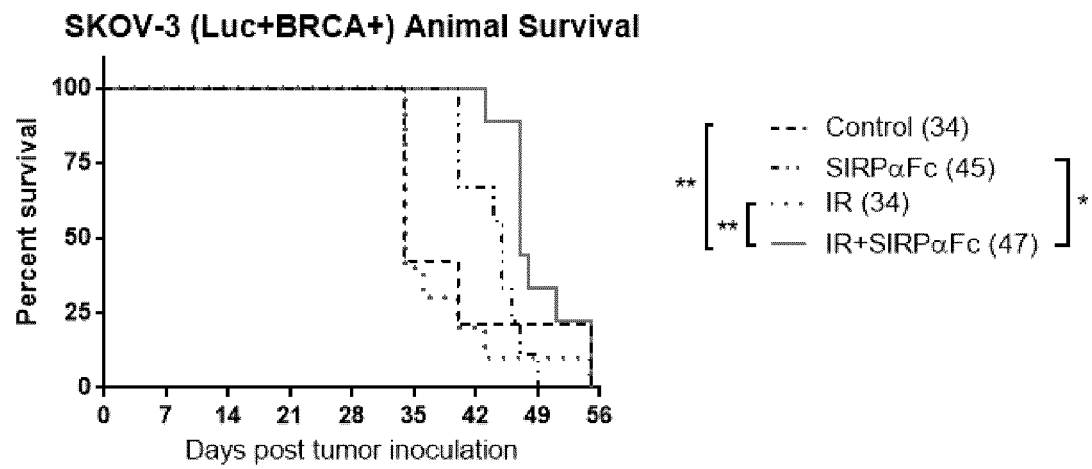
Figure 5B:
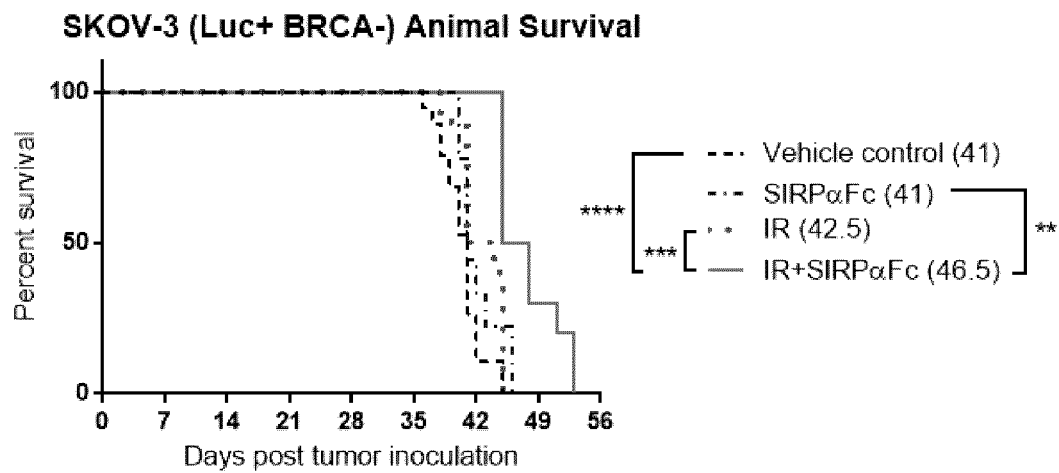

FIG. 5:
NOD/SCID mice were implanted intraperitoneally (IP) with luciferase expressing SKOV-3 cells, which were either BRCA competent (SKOV-3 Luc+BRCA+) or BRCA knock-down (SKOV-3 Luc+BRCA−). Mice were randomized using bioluminescence imaging (BLI) on day 6 following tumor inoculation. Treatment was initiated on day 7, which include (1) vehicle control, (2) SIRPαFc (10 mg/kg, 3 times/week, 3 weeks), (3) whole abdomen IR (2 fractions of 2 Gy on days 7 and 10, 4×4 cm collimator, 225 kVp, 13 mA), and (4) IR+SIRPαFc. (A) survival of mice bearing SKOV-3 Luc+BRCA+ tumors, (B) survival of mice bearing SKOV-3 Luc+BRCA-tumors. Median survival was indicated in the parentheses. The combination of IR and SIRPαFc resulted in significantly improved animal survival as compared to vehicle control in both tumor models.

DETAILED DESCRIPTION

The present treatment method combines a CD47 blocking agent, and radiation therapy, thereby improving the efficacy with which CD47+ disease cells and tumours are treated. Improved efficacy can manifest as a less-than-additive effect, wherein the effect of the combination is greater than the effect of each component alone, but less than the sum of the effects of both components, or it may be an additive effect, wherein the effect of the combination is equivalent to the sum of the effects of the components when used individually, or it may be a greater-than-additive effect, wherein the effect of the combination is greater than the sum of the effects of each component used alone. Greater-than-additive effects may also be described as synergistic. The improved efficacy of the combination can be determined by a number of methods known in the art. Improved efficacy can result in a statistically significant increase in the ability of the combination to inhibit the growth or proliferation or vitality of CD47+ disease cells when compared to the effect of each component alone. In embodiments, the effect is a greater than additive effect. Thus a treatment effective amount or dose of IR with SIRPαFc is preferably an amount or dose of the combination that gives an additive or greater than additive effect on the vitality of CD47+ disease cells, or on any other treatment-relevant parameter.

An agent that has CD47 blocking activity is an agent that interferes with and dampens or blocks signal transmission that results when CD47 interacts with macrophage-presented SIRPα. CD47-binding forms of human SIRPα are the preferred CD47 blocking agents for use in the combination herein disclosed. These agents are based on the extracellular region of human SIRPα. They comprise at least a part of the extracellular region of human SIRPα effective for CD47 binding affinity and specificity. CD47-binding forms of SIRPα include those SIRPα forms that lack the membrane anchoring component of SIRPα and/or the intracellular region of SIRPα. Different types of these useful forms of SIRPα are described in the literature and include those referenced in Novartis' WO 2010/070047, Stanford's WO2013/109752, and Trillium Therapeutics' WO2014/094122 (see also U.S. Pat. No. 9,969,789), as well as bispecific forms of these.

In a preferred embodiment, the CD47-binding form of SIRPα is an Fc fusion. More particularly, the CD47 blocking agent suitably comprises the human SIRPα protein, in a form fused directly, or indirectly, with an antibody constant region, or Fc (fragment crystallisable) Unless otherwise stated, the term "human SIRPα" as used herein refers to a wild type, endogenous, mature form of human SIRPα. In humans, the SIRPα protein is found in two major forms. One form, the variant 1 or V1 form, has the amino acid sequence set out as NCBI RefSeq NP_542970.1 (residues 27-504 constitute the mature form). Another form, the variant 2 or V2 form, differs by 13 amino acids and has the amino acid sequence set out in GenBank as CAA71403.1 (residues 30-504 constitute the mature form). These two forms of SIRPα constitute about 80% of the forms of SIRPα present in humans, and both are embraced herein by the term "human SIRPα". Also embraced by the term "human SIRPα" are the minor forms thereof that are endogenous to humans and have the same property of triggering signal transduction through CD47 upon binding thereto. The present disclosure is directed most preferably to the drug combinations that include the human SIRP variant 2 form, or V2.

In the present treatment combination, useful SIRPαFc fusion proteins comprise one of the three so-called immunoglobulin (Ig) domains that lie within the extracellular region of human SIRPα. More particularly, the present SIRPαFc proteins incorporate residues 32-137 of human SIRPα (a 106-mer), which constitute and define the IgV domain of the V2 form according to current nomenclature. This SIRPα sequence, shown below, is referenced herein as SEQ ID NO: 1.

```
                                              (SEQ ID NO: 1)
EELQVIQPDKSVSVAAGESAILHCTVTSLIPVGPIQWFRGAGPARE

LIYNQKEGHFPRVTTVSESTKRENMDFSISISNITPADAGTYYCVK

FRKGSPDTEFKSGA
```

In a preferred embodiment, the SIRPαFc fusion protein incorporates the IgV domain as defined by SEQ ID NO: 1, and additional, flanking residues contiguous within the SIRPα sequence. This preferred form of the IgV domain, represented by residues 31-148 of the V2 form of human SIRPα, is a 118-mer having SEQ ID NO: 2 shown below:

```
                                              (SEQ ID NO: 2)
EEELQVIQPDKSVSVAAGESAILHCTVTSLIPVGPIQWFRGAGPARE

LIYNQKEGHFPRVTTVSESTKRENMDFSISISNITPADAGTYYCVKF

RKGSPDTEFKSGAGTELSVRAKPS
```

A SIRPα fusion protein can incorporate an Fc region having effector function. Fc refers to "fragment crystallisable" and represents the constant region of an antibody comprised principally of the heavy chain constant region and components within the hinge region. Suitable Fc components thus are those having effector function. An Fc component "having effector function" is an Fc component having at least some effector function, such as at least some contribution to antibody-dependent cellular cytotoxicity or some ability to fix complement. Also, the Fc will at least bind to Fc receptors. These properties can be revealed using assays established for this purpose. Functional assays include the standard chromium release assay that detects target cell lysis. By this definition, an Fc region that is wild type IgG1 or IgG4 has effector function, whereas the Fc region of a human IgG4 mutated to eliminate effector function, such as by incorporation of an alteration series that includes Pro233, Val234, Ala235 and deletion of Gly236 (EU), is considered not to have effector function. In a preferred embodiment, the Fc is based on human antibody of the IgG1 isotype. In embodiments, the Fc region includes the lower hinge-CH2-CH3 domains.

In a specific embodiment, the Fc region is based on the amino acid sequence of a human IgG1 set out as P01857 in UniProtKB/Swiss-Prot, residues 104-330, and has the amino acid sequence shown below and referenced herein as SEQ ID NO: 3:

```
                                              (SEQ ID NO: 3)
DKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWL

NGKEYKCKVSNKALPAPIEKTISKAKGQPREPQVYTLPPSRDELTKN

QVSLTCLVKGFYPSDIAVEWESNGQPENNYKTTPPVLDSDGSFFLYS

KLTVDKSRWQQGNVFSCSVMHEALHNHYTQKSLSLSPGK*
```

Thus, in embodiments, the Fc region has either a wild type or consensus sequence of an IgG1 constant region. In alternative embodiments, the Fc region incorporated in the fusion protein is derived from any IgG1 antibody having a typical effector-active constant region. The sequences of such Fc regions can correspond, for example, with the Fc regions of any of the following IgG1 sequences (all referenced from GenBank), for example: BAG65283 (residues 242-473), BAC04226.1 (residues 247-478), BAC05014.1 (residues 240-471), CAC20454.1 (residues 99-320), BAC05016.1 (residues 238-469), BAC85350.1 (residues 243-474), BAC85529.1 (residues 244-475), and BAC85429.1 (residues 238-469).

In the alternative, the Fc region can be a wild type or consensus sequence of an IgG2 or IgG3 sequence, examples thereof being shown below:
a human IgG2, for example:

```
                                              (SEQ ID NO: 4)
APPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSN

KGLPAPIEKTISKTKGQPREPQVYTLPPSREEMTKNQVSLTCLVKGF

YPSDISVEWESNGQPENNYKTTPPMLDSDGSFFLYSKLTVDKSRWQQ

GNVFSCSVMHEALHNHYTQKSLSLSPGK,
``` as comprised in P01859 of the UniProtKB/Swiss-Prot database;
a human IgG3, for example:

```
                                              (SEQ ID NO: 5)
APELLGGPSVFLFPPKPKDTLMISRTPEVTCVVVDVSHEDPEVQFKWY

VDGVEVHNAKTKPREEQYNSTFRVVSVLTVLHQDWLNGKEYKCKVSNK

ALPAPIEKTISKTKGQPREPQVYTLPPSREEMTKNQVSLTCLVKGFYP

SDIAVEWESSGQPENNYNTTPPMLDSDGSFFLYSKLTVDKSRWQQGNI

FSCSVMHEALHNRFTQKSLSLSPGK,
``` as comprised in P01860 of the UniProtKB/Swiss-Prot database;

In other embodiments, the Fc region has a sequence of a wild type human IgG4 constant region. In alternative embodiments, the Fc region incorporated in the fusion protein is derived from any IgG4 antibody having a constant region with effector activity that is present but, naturally, is significantly less potent than the IgG1 Fc region. The sequences of such Fc regions can correspond, for example, with the Fc regions of any of the following IgG4 sequences: P01861 (residues 99-327) from UniProtKB/Swiss-Prot and CAC20457.1 (residues 99-327) from GenBank.

In a specific embodiment, the Fc region is based on the amino acid sequence of a human IgG4 set out as P01861 in UniProtKB/Swiss-Prot, residues 99-327, and has the amino acid sequence shown below and referenced herein as SEQ ID NO: 6:

```
                                              (SEQ ID NO: 6)
ESKYGPPCPSCPAPEFLGGPSVFLFPPKPKDTLMISRTPEVTCVVVDV

SQEDPEVQFNWYVDGVEVHNAKTKPREEQFNSTYRVVSVLTVLHQDWL

NGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRL

TVDKSRWQEGNVFSCSVMHEALHNHYTQKSLSLSLGK
```

In embodiments, the Fc region incorporates one or more alterations; usually not more than about 10, e.g., up to 5 such alterations, including amino acid substitutions that affect certain Fc properties. In one specific and preferred embodiment, the Fc region incorporates an alteration at position 228 (EU numbering), in which the serine at this position is substituted by a proline (S228P), thereby to stabilize the disulfide linkage within the Fc dimer. Other alterations within the Fc region can include substitutions that alter glycosylation, such as substitution of Asn297 by glycine or alanine; half-life enhancing alterations such as T252L, T253S, and T256F as taught in U.S. 62/777,375, and many others. Particularly useful are those alterations that enhance Fc properties while remaining silent with respect to conformation, e.g., retaining Fc receptor binding.

In a specific embodiment, and in the case where the Fc component is an IgG4 Fc, the Fc incorporates at least the S228P mutation, and has the amino acid sequence set out below and referenced herein as SEQ ID NO: 7:

(SEQ ID NO: 7)
ESKYGPPCPPCPAPEFLGGPSVFLFPPKPKDTLMISRTPEVTCVVVD

VSQEDPEVQFNWYVDGVEVHNAKTKPREEQFNSTYRVVSVLTVLHQD

WLNGKEYKCKVSNKGLPSSIEKTISKAKGQPREPQVYTLPPSQEEMT

KNQVSLTCLVKGFYPSDIAVEWESNGQPENNYKTTPPVLDSDGSFFL

YSRLTVDKSRWQEGNVFSCSVMHEALHNHYTQKSLSLSLGK

The CD47 blocking agent used in the treatment combination is thus preferably a SIRP fusion protein useful to inhibit the binding of human SIRPα and human CD47, thereby to inhibit or reduce transmission of the signal mediated via SIRPα-bound CD47, the fusion protein comprising a human SIRPα component and, fused therewith, an Fc component, wherein the SIRPα component comprises or consists of a single IgV domain of human SIRPα V2 and the Fc component is the constant region of a human IgG having effector function.

In one embodiment, the CD47 blocking agent comprises a SIRPα component consisting at least of residues 32-137 of the V2 form of wild type human SIRPα, i.e., SEQ ID NO: 1. In a preferred embodiment, the SIRPα component consists of residues 31-148 of the V2 form of human SIRPα, i.e., SEQ ID NO: 2. In another embodiment, the Fc component is the Fc component of the human IgG1 designated P01857, and in a specific embodiment has the amino acid sequence that incorporates the lower hinge-CH2-CH3 region thereof i.e., SEQ ID NO: 3.

In a preferred embodiment, therefore, the SIRPαFc fusion protein is provided and used in a secreted dimeric fusion form, wherein the fusion protein incorporates a SIRPα component having SEQ ID NO: 1 and preferably SEQ ID NO: 2 and, fused therewith, an Fc region having effector function and having SEQ ID NO: 3. When the SIRPα component is SEQ ID NO: 1, this fusion protein comprises SEQ ID NO: 8, shown below:

(SEQ ID NO: 8)
EELQVIQPDKSVSVAAGESAILHCTVTSLIPVGPIQWFRGAGPAREL

IYNQKEGHFPRVTTVSESTKRENMDFSISISNITPADAGTYYCVKFR

KGSPDTEFKSGAGTELSVRAKPSDKTHTCPPCPAPELLGGPSVFLFP

PKPKDTLMISRTPEVTCVVVDVSHEDPEVKFNWYVDGVEVHNAKTKP

REEQYNSTYRVVSVLTVLHQDWLNGKEYKCKVSNKALPAPIEKTISK

-continued
AKGQPREPQVYTLPPSRDELTKNQVSLTCLVKGFYPSDIAVEWESNG

QPENNYKTTPPVLDSDGSFFLYSKLTVDKSRWQQGNVFSCSVMHEAL

HNHYTQKSLSLSPGK*

When the SIRPα component is SEQ ID NO: 2, this fusion protein comprises SEQ ID NO: 9, (also referred to herein as TTI-621) shown below:

(SEQ ID NO: 9)
EEELQVIQPDKSVSVAAGESAILHCTVTSLIPVGPIQWFRGAGPAREL

IYNQKEGHFPRVTTVSESTKRENMDFSISISNITPADAGTYYCVKFRK

GSPDTEFKSGAGTELSVRAKPSDKTHTCPPCPAPELLGGPSVFLFPPK

PKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQ

KSLSLSPGK.

This is also referred to herein as TTI-621 and as SIRPαFc in the examples.

In alternative embodiments, the Fc component of the fusion protein is based on an IgG4, and preferably an IgG4 that incorporates the S228P mutation. In the case where the fusion protein incorporates the preferred SIRPα IgV domain of SEQ ID NO: 2, the resulting IgG4-based SIRPα-Fc protein has SEQ ID NO 10, shown below (also referred to as TTI-622):

(SEQ ID NO: 10)
EEELQVIQPDKSVSVAAGESAILHCTVTSLIPVGPIQWFRGAGPAREL

IYNQKEGHFPRVTTVSESTKRENMDFSISISNITPADAGTYYCVKFRK

GSPDTEFKSGAGTELSVRAKPSESKYGPPCPPCPAPEFLGGPSVFLFP

PKPKDTLMISRTPEVTCVVVDVSQEDPEVQFNWYVDGVEVHNAKTKPR

EEQFNSTYRVVSVLTVLHQDWLNGKEYKCKVSNKGLPSSIEKTISKAK

GQPREPQVYTLPPSQEEMTKNQVSLTCLVKGFYPSDIAVEWESNGQPE

NNYKTTPPVLDSDGSFFLYSRLTVDKSRWQEGNVFSCSVMHEALHNHY

TQKSLSLSLGK

In preferred embodiment, the fusion protein comprises, as the SIRPα IgV domain of the fusion protein, a sequence that is SEQ ID NO: 2. A preferred SIRPαFc is SEQ ID NO: 9. Another preferred SIRPαFc is SEQ ID NO: 10.

The SIRPα sequence incorporated within the CD47 blocking agent can be varied from the wild type sequence, as described in the literature. That is, useful substitutions within SIRPα include one or more of the following: L4V/I, V6I/L, A21V, V27I/L, I31T/S/F, E47V/L, K53R, E54Q, H56P/R, S66T/G, K68R, V92I, F94V/L, V63I, and/or F103V (SEQ ID NO: 15).

In embodiments, the CD47 blockade drug is a variant of human SIRPα having higher binding affinity for human CD47 than wild type SIRPα. In a specific embodiment, the variant SIRPα has the sequence:

```
                                             (SEQ ID NO: 11)
EEELQIIQPDKSVSVAAGESAILHCTITSLFPVGPIQWFRGAGPARVL

IYNQRQGPFPRVTTVSETTKRENMDFSISISNITPADAGTYYCIKFRK

GSPDTEFKSGAGTELSVRAKP
```

This SIRPα variant comprises the following amino acid substitutions relative to wild type SIRPα: V6I+V27I+I31F+E47V+K53R+E54Q+H56P+S66T+V92I. In a specific embodiment, this variant SIRPα sequence can be fused with a mutated IgG4 Fc region including a Ser228Pro (EU) having virtually no effector function, to yield a CD47 blockade drug having the sequence shown in SEQ ID NO: 12:

```
                                             (SEQ ID NO: 12)
EEELQIIQPDKSVSVAAGESAILHCTITSLFPVGPIQWFRGAGPARVL

IYNQRQGPFPRVTTVSETTKRENMDFSISISNITPADAGTYYCIKFRK

GSPDTEFKSGAGTELSVRAKPSESKYGPPCPPCPAPPVAGPSVFLFPP

KPKDTLMISRTPEVTCVVVDVSQEDPEVQFNWYVDGVEVHNAKTKPRE

EQFNSTYRVVSVLTVLHQDWLNGKEYKCKVSNKGLPSSIEKTISKAKG

QPREPQVYTLPPSQEEMTKNQVSLTCLVKGFYPSDIAVEWESNGQPEN

NYKTTPPVLDSDGSFFLYSRLTVDKSRWQEGNVFSCSVMHEALHNHYT

QKSLSLSLGK*
```

In the SIRPαFc fusion protein, the SIRPα component and the Fc component are fused, either directly or indirectly, to provide a single chain polypeptide that is ultimately produced as a dimer in which the single chain polypeptides are coupled through intrachain disulfide bonds formed within the Fc region. The nature of the fusing region is not critical. The fusion may be direct between the two components, with the SIRP component constituting the N-terminal end of the fusion and the Fc component constituting the C-terminal end. Alternatively, the fusion may be indirect, through a linker comprised of one or more amino acids, desirably genetically encoded amino acids, such as two, three, four, five, six, seven, eight, nine or ten amino acids, or any number of amino acids between 5 and 100 amino acids, such as between 5 and 50, 5 and 30 or 5 and 20 amino acids. A linker may comprise a peptide that is encoded by DNA constituting a restriction site, such as a BamHI, ClaI, EcoRI, HindIII, PstI, SalI and XhoI site and the like.

The linker amino acids typically and desirably have some flexibility to allow the Fc and the SIRP components to adopt their active conformations. Residues that allow for such flexibility typically are Gly, Asn and Ser, so that virtually any combination of these residues (and particularly Gly and Ser) within a linker is likely to provide the desired linking effect. In one example, such a linker is based on the so-called G4S sequence (Gly-Gly-Gly-Gly-Ser, SEQ ID NO: 14) which may repeat as (G4S)n where n is 1, 2, 3 or more, or is based on (Gly)n, (Ser)n, (Ser-Gly)n or (Gly-Ser)n and the like. In another embodiment, the linker is GTELSVRAKPS (SEQ ID NO: 13). This sequence constitutes SIRPα sequence that C-terminally flanks the IgV domain (it being understood that this flanking sequence could be considered either a linker or a different form of the IgV domain when coupled with the IgV minimal sequence described above). It is necessary only that the fusing region or linker permits the components to adopt their active conformations, and this can be achieved by any form of linker useful in the art.

As noted, the SIRPαFc fusion is useful to inhibit interaction between SIRPα and CD47, thereby to block signalling across this axis. Stimulation of SIRPα on macrophages by CD47 is known to inhibit macrophage-mediated phagocytosis by deactivating myosin-II and the contractile cytoskeletal activity involved in pulling a target into a macrophage. Activation of this cascade is therefore important for the survival of CD47+ disease cells, and blocking this pathway enables macrophages to eradicate or at least reduce the CD47+ disease cell population.

For administration, the SIRPαFc is formulated with a pharmaceutically acceptable carrier, and in a therapeutically effective amount. Pharmaceutically acceptable carriers include any and all solvents, dispersion media, coatings, antibacterial and antifungal agents, isotonic and absorption delaying agents, and the like that are physiologically compatible and useful in the art of protein/antibody formulation. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent. Solutions that are suitable for intravenous administration, such as by injection or infusion, are particularly useful.

As used herein, "therapeutically effective amount" refers to an amount of the CD47 blocking agent, e.g., SIRPαFc, which is effective, at dosages and for a particular period of time necessary, to achieve the desired therapeutic result. Similarly, a "medicinally" useful amount is an amount useful for any medicinal purpose. The SIRPαFc fusion protein can be administered to the subject through any of the routes established for protein delivery, in particular intravenous, intradermal and subcutaneous injection or infusion, or by oral or nasal administration. In one embodiment, the SIRPαFc is administered by injection or infusion directly into the tumour. For administration to a subject presenting with CD47+ disease cells, the dose for the CD47 blockade drug will be within the range from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 0.1-100 mg/kg. For direct intratumoural injection, a unit dose of 1-5 mg is suitable, per tumour.

The present treatment combination comprises both a CD47 blocking agent that is a CD47-binding form of a SIRPα, as just described, and radiation therapy, known also as radiotherapy or RT. In an embodiment, the RT is external beam radiotherapy (EBR). In an alternative embodiment, the RT is brachytherapy.

Radiotherapy is the treatment of cancer and other diseases with ionizing radiation. It is a very well established approach to the treatment of numerous types of cancer, and has been refined so that each cancer type typically receives an RT treatment regimen tailored for that particular cancer. Ionizing radiation deposits energy that injures or destroys cells in the area being treated by damaging their genetic material, making it impossible for these cells to continue to grow. Radiotherapy can be used to treat localized solid tumors, such as cancers of the ovary, prostate, skin, tongue, larynx, brain, breast, or cervix. It can also be used to treat so-called blood cancers including leukemia and lymphoma (cancers of the blood-forming cells and lymphatic system, respectively).

In an embodiment, the RT is external-beam radiation (EBR) therapy. Conventional external beam radiation therapy (2DXRT) is delivered via two-dimensional beams using kilovoltage therapy X-ray units or medical linear accelerators which generate high energy x-rays. 2DXRT mainly consists of a single beam of radiation delivered to the patient from several directions: often front or back, and both sides. External-beam radiation therapy is most often delivered in the form of photon beams (either x-rays or gamma rays). Many types of external-beam radiation therapy are delivered using a linear accelerator that uses electricity to form a stream of fast-moving subatomic particles. Subjects can receive external-beam radiation therapy in daily treatment sessions over the course of several weeks. The number of treatment sessions depends on many factors, including the total radiation dose that will be given. Another useful type of external-beam radiation therapy is 3-dimensional conformal radiation therapy (3D-CRT). 3D-CRT uses sophisticated computer software and advanced treatment machines to deliver radiation to very precisely shaped target areas.

Still other methods of external-beam radiation therapy are useful in the present treatment method. These include intensity-modulated radiation therapy (IMRT), which uses hundreds of tiny radiation beam-shaping devices, i.e., collimators, to deliver a dose of radiation. The collimators can be stationary or can move during treatment, allowing the intensity of the radiation beams to change during treatment sessions, so that different areas of a tumor or nearby tissues can be hit with different doses of radiation. IMRT can be used to increase the radiation dose to treatment areas.

In use, each of the two treatment modalities in the present method will be utilized as it would be used in monotherapy, i.e., as it would be used independently of its combination with any other agent. Methods of administration and dosing will be consistent with established applications as a monotherapeutic, so that each modality provides, where it can, an anti-cancer benefit that will be enhanced when the modalities are combined in treating a given subject.

In embodiments, subjects will receive most types of external-beam radiation therapy up to 5 days a week for several weeks. One dose (a single fraction) of the total planned dose of radiation is given each day. Occasionally, two treatments a day are given. Most types of external-beam radiation therapy are given in once-daily fractions, so that damage to normal tissue is minimized and to increase the likelihood that cancer cells are exposed to radiation at the points in the cell cycle when they are most vulnerable to DNA damage. Fractionation of a dosing schedule is now common, including accelerated fractionation where treatment is given in larger daily or weekly doses to reduce the number of weeks of treatment; hyperfractionation whereby smaller doses of radiation are given more than once a day; and hypofractionation by which larger doses are given once a day or less often to reduce the number of treatments.

Fractionation regimens are individualised between different radiation therapy centers and even between individual doctors. In North America, Australia, and Europe, the typical fractionation schedule for adults is 1.8 to 2 Gy per day, five days a week. In some cancer types, prolongation of the fraction schedule over too long can allow for the tumor to begin repopulating, and for these tumor types, including head-and-neck and cervical squamous cell cancers, radiation treatment is preferably completed within a certain amount of time. For children, a typical fraction size may be 1.5 to 1.8 Gy per day, as smaller fraction sizes are associated with reduced incidence and severity of late-onset side effects in normal tissues.

In some cases, two fractions per day are used near the end of a course of treatment. This schedule, known as a concomitant boost regimen or hyperfractionation, is used on tumors that regenerate more quickly when they are smaller. In particular, tumors in the head-and-neck demonstrate this behavior.

Hypofractionation is a radiation treatment in which the total dose of radiation is divided into large doses. Typical doses vary significantly by cancer type, from 2.2 Gy/fraction to 20 Gy/fraction. The logic behind hypofractionation is to lessen the possibility of the cancer returning by not giving the cells enough time to reproduce and also to exploit the unique biological radiation sensitivity of some tumors. One commonly treated site where there is very good evidence for such treatment is in breast cancer. Short course hypofractionated treatments over 3-4 weeks e.g. 40 Gy in 15 fractions or 42.5 Gy in 16 fractions, have been shown to be as effective as more protracted 5-6 week treatments with respect to cancer control.

An alternative fractionation schedule is Continuous Hyperfractionated Accelerated Radiation therapy. CHART is used to treat lung cancer and consists of three smaller fractions per day. Another increasingly well-known alternative fractionation schedule, used to treat breast cancer, is called Accelerated Partial Breast Irradiation (APBI). APBI can be performed with external beam radiation. APBI involves two high-dose fractions per day for five days, compared to whole breast irradiation, in which a single, smaller fraction is given five times a week over a six-to-seven-week period.

Thus, for radiotherapy, dosing levels and regimens will be determined by the type, location and stage of cancer being treated. The dose can be photon- or proton-based and expressed either in Roentgens or in Gray units, to indicate the exposed dose (Rn) or the absorbed dose (Gy) of radiation. The Gray is a derived unit of ionizing radiation dose, which is a measure of the amount of radiation energy absorbed by 1 kilogram of human tissue. It is related to the rad, which is 0.01 Gy. Generally, appropriate dosing will range from about 1 to about 300 Gy per exposure. Total dosages per exposure can vary from about 1 to about 500 Gy and particularly 40-70 Gy.

By definition, one roentgen of air kerma (kinetic energy released per unit mass) deposits 0.00877 grays (0.877 rads) of absorbed dose in dry air, or 0.0096 Gy (0.96 rad) in soft tissue. One roentgen (air kerma) of X-rays may deposit anywhere from 0.01 to 0.04 Gy (1.0 to 4.0 rad) in bone depending on the beam energy. Dosage ranges for X-rays in the present method range from daily doses of 50 to 200 roentgens as well as all intermediate dosage levels therebetween for prolonged periods of time such as 3 to 4 weeks, to single doses of 2000 to 6000 roentgens (including, but not limited to 2500, 3000, 3500, 4000, 4500, 5000, and 5500 roentgens).

External beam radiotherapy schedules used in accordance with the present method can also vary. In certain embodiments, a particular schedule can comprise daily treatments about 5 times per week for about six to about seven weeks or can comprise about twice daily treatments for about two to about three weeks.

In alternative embodiments, the radiation therapy can be brachytherapy. In brachytherapy, a source of radiation source is placed inside or next to the area requiring treatment. It is used as a treatment particularly for breast, cervical, prostate and skin cancer. Brachytherapy involves the precise placement of short-range radiation-sources (radioisotopes) directly at the tumour. These are enclosed in a protective capsule or wire, which allows the ionizing radiation to treat and kill surrounding tissue.

A course of brachytherapy thus begins with placement of the radiation source and ends with its removal or when the source radiation expires. The dose rate of brachytherapy refers to the level or 'intensity' with which the radiation is delivered to the surrounding medium and is expressed in Grays per hour (Gy/h). Low-dose rate (LDR) brachytherapy involves implanting radiation sources that emit radiation at a rate of up to 2 Gy/h. LDR brachytherapy is commonly used for cancers of the oral cavity, oropharynx, sarcomas and prostate. Medium-dose rate (MDR) brachytherapy is characterized by a medium rate of dose delivery, ranging between 2 Gy/h to 12 Gy/h. In high-dose rate (HDR) brachytherapy, the rate of dose delivery exceeds 12 Gy/h. The most common applications of HDR brachytherapy are in tumours of the cervix, esophagus, lungs, breasts and prostate.

Pulsed-dose rate (PDR) brachytherapy involves short pulses of radiation, typically once an hour, to simulate the overall rate and effectiveness of LDR treatment. Typical tumour sites treated by PDR brachytherapy are gynaecological and head and neck cancers.

The placement of radiation sources in the target area can be temporary or permanent. Temporary brachytherapy involves placement of radiation sources for a set duration (usually a number of minutes or hours) before being withdrawn. Treatment duration will depend on many factors, such as the required rate of dose delivery and the type, size and location of the cancer. In LDR and PDR brachytherapy, the source stays in place up to 24 hours and is then removed, while in HDR brachytherapy this time is typically just a few minutes Permanent brachytherapy, also known as seed implantation, involves placing small LDR radioactive seeds or pellets (about the size of a grain of rice) in the tumour or treatment site and leaving them there permanently to gradually decay. Over a period of weeks or months, the radiation emitted by the sources will decline to almost zero. The inactive seeds then remain in the treatment site but with no lasting effect.

Commonly used sources of brachytherapy radiation include Cesium-131, Cesium-137, Cobalt-60, Iridium-192, Iodine-125, Palladium-103, Ruthenium-106 and Radium-226.

As noted, in the present treatment method, the CD47 blocking agent is a CD47-binding form of human SIRPα that is used in combination with radiation therapy to treat CD47+ diseases and particularly hyperproliferative disease and especially cancer. In terms of an anti-cancer effect, such as a depletion of CD47+ cancer cells, the treatment modalities cooperate to provide an enhanced reduction in cancer cell vitality, activity or mortality. The cooperative or enhanced effect of the combination can also be revealed in the context of other parameters, such as a reduction in cancer cell viability, size, number, or distribution, or improvement in overall burden of a tumour. It can also manifest as an increased infiltration of tumours by macrophages or any other phagocytic cell type.

The treatment modalities in the present combination can be delivered sequentially or, essentially at the same time, i.e. concurrently. In embodiments, the RT can be given before administration of SIRPαFc. In general, the delivery of one modality relative the other in temporal terms refers to the delivery of one modality in terms of one course of treatment, versus the delivery of the other modality in terms of its course of treatment. Thus, concurrent delivery means that courses of treatment overlap, whereas successive delivery means that courses of treatment do not overlap physically.

In some embodiments, EBR therapy can be administered within about 1-60 minutes, or 2-48 hours or more prior to and/or after administering the CD47 blocking agent. In other embodiments, radiation therapy can be administered within from about 1 day to about 21 days prior to and/or after administering the CD47 blocking agent. In some embodiments, the time period for treatment can be extended significantly, however, where several weeks (e.g., about 1, about 2, about 3, about 4, about 5, about 6, about 7, or about 8 weeks or more) lapse between the administration of the CD47 blocking agent and the radiation therapy. It is important only that the effect of one agent is present in the subject when the other agent is administered. It is desirable in one embodiment that the agents are used concurrently and that their activities overlap actively within the subject undergoing treatment. In the context of brachytherapy, the modalities can be used concurrently, meaning that internal radiation is in place during a course of treatment with the CD47-binding agent, or the CD47-binding agent treatment can be administered to a subject that has completed a course of brachytherapy.

As revealed in the results shown in the Examples herein, it is believed that the benefit of combining radiotherapy and CD47 blockade therapy lies in elevating the number of macrophages that infiltrate tumours to deplete disease cells, with SIPRα-Fc augmenting the anti-tumor immunity induced by RT. The present method thus can be characterized as a method for increasing the number of macrophages present within a tumour, comprising treating the tumour with a combination of SIRPαFc and radiation to cause depletion of disease cells within the tumour.

In a further aspect, there is provided an article of manufacture containing the SIRPαFc drug in an amount useful for the treatment of the disorders described herein is provided. The article of manufacture comprises the SIRPαFc in a container and further comprises an indication or instruction, such as a label affixed to the container or included with the article that the SIRPαFc is for use in combination with radiation therapy. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or vial having a stopper pierceable by a hypodermic injection needle). The article of manufacture may further comprise a second container comprising a pharmaceutically-acceptable buffer, such as phosphate-buffered saline, Ringer's solution and dextrose solution. It may further include other matters desirable from a commercial and use standpoint, including other buffers, diluents, filters, needles, syringes, and package inserts with instructions for use.

The present treatment combination is useful to treat a variety of CD47+ disease cells. These include particularly CD47+ cancer cells, including liquid and solid tumours. The term "CD47+" is used with reference to the phenotype of cells targeted for binding by the CD47 blocking agent. Cells that are CD47+ can be identified by flow cytometry using CD47 antibody as the affinity ligand. CD47 antibodies that are labeled appropriately are available commercially for this use (for example, the antibody product of clone B6H12 is available from eBioscience). The cells examined for CD47 phenotype can include standard tumour biopsy samples including particularly blood samples taken from the subject suspected of harbouring endogenous CD47+ cancer cells. CD47 disease cells of particular interest as targets for therapy with the present fusion proteins are those that "over-express" CD47. These CD47+ cells typically are disease cells, and present CD47 at a density on their surface that exceeds the normal CD47 density for a cell of a given type. CD47 overexpression will vary across different cell types, but is meant herein to refer to any CD47 level that is determined, for instance by flow cytometry as exemplified herein or by immunostaining or by gene expression analysis or the like, to be greater than the level measurable on a counterpart cell having a CD47 phenotype that is normal for that cell type.

The types of ovarian cancer that can be treated with the present treatment combination include those within the three major categories, according to the kind of cells from which they were formed, i.e., (1) epithelial tumors that arise from cells that line or cover the ovaries; (2) germ cell tumors that originate from cells that are destined to form eggs within the ovaries; and (3) sex cord-stromal cell tumors that begin in the connective cells that hold the ovaries together and produce female hormones. Also included are tumors that are adjacent to ovarian tissues, such as extraovarian peritoneal carcinoma (intraperitoneal carcinomatosis), the common epithelial tumors including serous, endometrioid, mucinous, and clear cell tumors—that include benign (noncancerous) or malignant (cancerous) tumors.

Also treatable with the present treatment combination are the rare types of ovarian tumours, such as Brenner tumors, undifferentiated tumors, and transitional cell tumors as well as germ cell tumours that are formed from egg-making cells within the ovaries.

In other embodiments, the treatment combination can be used to inhibit the growth or proliferation of hematological cancers. As used herein, "hematological cancer" refers to a cancer of the blood, and includes leukemia, lymphoma and myeloma among others. "Leukemia" refers to a cancer of the blood, in which too many white blood cells that are ineffective in fighting infection are made, thus crowding out the other parts that make up the blood, such as platelets and red blood cells. It is understood that cases of leukemia are classified as acute or chronic. Certain forms of leukemia may be, by way of example, acute lymphocytic leukemia (ALL); acute myeloid leukemia (AML); chronic lymphocytic leukemia (CLL); chronic myelogenous leukemia (CML); myeloproliferative disorder/neoplasm (MPDS); and myelodysplastic syndrome. "Lymphoma" may refer to T cell lymphoma and B cell lymphoma, Hodgkin's lymphoma, both indolent and aggressive non-Hodgkin's lymphoma, Burkitt's lymphoma, and follicular lymphoma (small cell and large cell), among others. Myeloma may refer to multiple myeloma (MM), giant cell myeloma, heavy-chain myeloma, and light chain or Bence-Jones myeloma.

In some embodiments, the hematological cancer treated with the treatment combination is a CD47+ leukemia, preferably selected from acute lymphocytic leukemia, acute myeloid leukemia, chronic lymphocytic leukemia, chronic myelogenous leukemia, and myelodysplastic syndrome, preferably, acute myeloid leukemia.

In other embodiments, the hematological cancer treated with the treatment combination is a CD47+ lymphoma or myeloma selected from a T cell lymphoma including cutaneous T cell lymphoma, Sezary Syndrome and mycosis fungoides, Hodgkin's lymphoma, both indolent and aggressive non-Hodgkin's lymphoma, Burkitt's lymphoma, B cell lymphoma, follicular lymphoma (small cell and large cell), multiple myeloma (MM), giant cell myeloma, heavy-chain myeloma, and light chain or Bence-Jones myeloma as well as leimyosarcoma. In some embodiments, the hematological cancer is diffuse large B-cell lymphoma (DLBCL) or peripheral T cell lymphoma (PTCL)

In another embodiment, the treatment combination is used to treat ovarian cancer. In a further embodiment, the combination is used to treat lung cancer. In another embodiment, the treatment combination is used to treat melanoma.

It will be appreciated that the radiosensitivity of the cancer can be enhanced by giving certain radiosensitizing drugs during a course of radiation therapy. Examples of radiosensitizers include: cisplatin, nimorazole, and cetuximab, among many others.

In some embodiments, the CD47 blockade therapeutic, described herein as a polypeptide (e.g., a fusion protein or an antibody), is administered as a "nucleotide equivalent" (a CD47 blockade polynucleotide) via gene therapy methods. In one embodiment, the CD47 blockade polynucleotide is encoded in a plasmid or vector. Accordingly, in exemplary aspects, the CD47 blockade peptides are used or administered by way of administering a CD47 blockade nucleic acid comprising a nucleotide sequence encoding a CD47 blockade polypeptide described herein. In exemplary instances, the nucleic acid comprises a nucleotide sequence which encodes any of the CD47 blockade polypeptides described herein. The nucleic acid or polynucleotide generally is a polymer of DNA or RNA, which can be single-stranded or double-stranded, which can contain natural, non-natural, or altered nucleotides, and which can contain a natural, non-natural or altered inter-nucleotide linkage, such as a phosphoroamidate linkage or a phosphorothioate linkage, instead of the phosphodiester found between the nucleotides of an unmodified oligonucleotide. Exemplary polynucleotide constructs are described in U.S. Pat. No. 9,979,789, incorporated herein by reference. In some variations, the CD47 blockade polynucleotide (or vector) includes sequence encoding a signal peptide operably linked to sequence encoding the CD47 blockade therapeutic, to direct/facilitate secretion of the CD47 blockade therapeutic from transformed/transfected cells.

In exemplary aspects, the nucleic acids are constructed based on chemical synthesis and/or enzymatic ligation reactions. See, for example, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, N.Y., 1994. For example, a nucleic acid can be chemically synthesized using naturally occurring nucleotides or modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Nucleic acids can be expanded using both recombinant means and synthetic means (e.g., PCR).

In some variations, the nucleic acids are incorporated into a vector. As used herein, a "vector" or "expression vector" is any molecule or moiety which transports, transduces or otherwise acts as a carrier of a heterologous molecule such as the nucleic acids encoding a CD47 blockade polypeptide. In exemplary aspects, the vector is a genetically-modified polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell.

Suitable vectors include those designed for propagation and expansion or for expression or both, such as plasmids and viruses. Preferably, the vector is a viral vector, e.g., a retroviral vector. A "viral vector" is a vector which comprises one or more polynucleotide regions encoding or comprising payload molecule of interest, e.g., a transgene, a polynucleotide encoding a polypeptide or multi-polypeptide. In exemplary aspects, the viral vector is a vaccinia virus vector, a poxvirus vector, an adenovirus vector, an adeno-associated virus vector, or a herpes simplex virus vector.

Desirably, the polynucleotide or vector comprises regulatory sequences, such as transcription and translation initiation and termination codons. Furthermore, in some variations, a promoter is used that is selective of specific for the types of cells to which the CD47 blockade polynucleotide is to be targeted, or which is inducible, or which is cycle-specific. In some variations, the promoter is a viral promoter, e.g., a cytomegalovirus (CMV) promoter, an SV40 promoter, an RSV promoter, CAG promoter and a promoter found in the long-terminal repeat of the murine stem cell virus. The vectors can be designed for transient expression or stable expression. Also, the vectors can be made for constitutive expression or for inducible expression.

Methods of delivering nucleic acids for expression in cells are known in the art and include for example, lipid delivery using cationic lipids or other chemical methods (e.g., calcium phosphate precipitation, DEAE-dextran, polybrene), electroporation, or viral delivery. See, e.g., Sambrook and Russell, Molecular Cloning: A Laboratory Manual, 3rd ed. Cold Spring Harbor Press, Cold Spring Harbor, N.Y. (2001), Nayerossadat et al., Adv Biomed Res 1: 27 (2012); and Hesier, William (ed.), Gene Delivery to Mammalian Cells, Vol 1., Non-viral Gene Transfer Techniques, Methods in Molecular Biology, Humana Press, (2004).

EXAMPLES

The combination of RT and a CD47-blocking agent SIRPαFc (SEQ #9) was examined in xenograft tumor models.

Materials and Methods

The in vivo efficacy of radiation therapy (RT), SIRPαFc, and RT+SIRPαFc was evaluated in subcutaneous B cell lymphoma (SUDHL-6) and solid tumor xenografts, including the radio-insensitive A549 lung adenocarcinoma (subcutaneous), and SKOV-3 ovarian adenocarcinoma (intraperitoneal). For subcutaneous tumor models, SIRPαFc (10 mg/kg) or vehicle was administered intratumourally 30 minutes prior to radiotherapy, 3 times per week for 3-4 weeks. Tumors were locally irradiated using an image-guided small animal irradiator (225 kVp, 13 mA) at a dose of 4-6 Gy for 3 fractions. Tumor volumes were monitored using standard caliper measurement. Tumor-associated macrophages were quantitatively assessed using flow cytometry and immunohistochemistry. For intraperitoneal tumor models of ovarian cancer, SIRPαFc (10 mg/kg) or vehicle was administered intraperitoneally 60 minutes prior to radiotherapy, 3 times per week for 3 weeks. Mice were treated with whole abdomen radiation (WAR) using image-guided X-ray IR. Briefly, mice were injected intraperitoneally (i.p.) with 100 mg/kg of D-luciferin 5 min prior to BLI acquisition. The mice were positioned on a stage and imaged by BLI followed by 2-D CT under anesthesia. Superimposed BLI and CT images were used to guide the radiation beam to the abdomen, with all the tumors included in the collimated area (4×4 cm). IR was conducted at 225 kVp and 13 mA with a copper filter. The isocenter of the radiation beam was set at 0.5 cm above the stage. The irradiation regimen was 2 fractions of 2 Gy on days 7 and 10. Systemic toxicity of the treatments was evaluated by body weight change.

Results

In both SU-DHL-6 and A549 tumor models, RT+SIRPαFc had a more profound effect on tumor control than RT alone. In SU-DHL-6, 88% (7/8) of mice treated with both SIRPαFc and external beam radiation were tumor-free at the end of the study whereas none were tumor-free when treated with RT or SIRPαFc alone, although there was tumor growth delay with each individual therapy compared to vehicle. RT+SIRPαFc led to an increased infiltration of macrophages at the tumor sites in SU-DHL-6. Statistically significant tumor control was also observed in A549 tumor bearing mice treated with RT+SIRPαFc compared to either treatment alone. No toxicity was observed for localized RT on the tumors and the combination of RT and SIRPαFc. In intraperitoneal tumor models of BRCA competent and knockdown SKOV-3, as measured by animal survival, statistically significant tumor control was achieved by RT+SIRPαFc, compared to vehicle control and RT alone. As measured by body weight change, no chronic toxicity was observed for whole abdomen RT and its combination with SIRPαFc.

As shown in the Figures, SIRPαFc increases phagocytosis of irradiated tumor cells by macrophages. It also enhances the anti-tumor effect of radiation therapy in xenograft tumor models of SU-DHL-6 (B lymphoma), A549 (lung adenocarcinoma), and BRCA competent as well as knockdown SKOV-3 (ovarian adenocarcinoma). The combination of SIRPαFc and radiation leads to elevated macrophage infiltration at the tumor sites. Sequencing of radiation and SIRPαFc impacts the efficacy of treatment, with concurrent SIRPαFc and IR being the most effective, followed by IR administered prior to SIRPαFc, and lastly, SIRPαFc prior to IR. These in vivo results show that concurrent radiation and CD47 blockade using SIRPαFc, e.g. administration of SIRPαFc during a course of radiation, or vice versa, can enhance tumor control and is a viable combination therapy that is superior to either treatment alone in terms of anti-cancer efficacy.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

We claim:

1. A method for treating a subject presenting with CD47+ disease cells, comprising administering to the subject a treatment-effective combination of a CD47 blocking agent and radiation, wherein the radiation is external beam radiation, and wherein the CD47 blocking agent comprises an Fc fusion protein comprising the IgV region of soluble human signal regulatory protein alpha (SIRPα) variant 2.

2. The method according to claim 1, wherein the subject is human.

3. The method according to claim 1, wherein the CD47 blocking agent comprises SEQ ID NO: 9.

4. The method according to claim 1, wherein the CD47 blocking agent comprises SEQ ID NO: 10.

5. The method according to claim 1, wherein the CD47 blocking agent is formulated with a pharmaceutically acceptable carrier.

6. The method according to claim 1, wherein the subject presents with CD47+ cancer cells that are blood cancer cells or solid tumour cells.

7. The method according to claim 6, wherein the cancer cells are blood cancer cells.

8. The method according to claim 7, wherein the blood cancer cells are cells of a leukemia selected from acute lymphocytic leukemia; acute myeloid leukemia; chronic lymphocytic leukemia; chronic myelogenous leukemia; myeloproliferative disorder/neoplasm; and myelodysplastic syndrome.

9. The method according to claim 7, wherein the blood cancer cells are cells of a lymphoma selected from a T cell lymphoma, cutaneous T cell lymphoma, Sezary Syndrome, mycosis fungoides, Hodgkin's lymphoma, indolent non-Hodgkin's lymphoma, aggressive non-Hodgkin's lymphoma, Burkitt's lymphoma, small cell follicular lymphoma, and large cell follicular lymphoma.

10. The method according to claim 7, wherein the blood cancer cells are cells of a myeloma selected from multiple myeloma (MM), giant cell myeloma, heavy-chain myeloma, light chain myeloma, and Bence-Jones myeloma.

11. The method according to claim 6, wherein the CD47+ cancer cells are cells of an ovarian cancer or a lung cancer.

12. The method according to claim 1, wherein the CD47 blocking agent and the radiation treatment are administered concurrently to the subject.

13. The method according to claim 1, wherein a course of treatment with the CD47 blocking agent overlaps with a course of the radiation treatment.

14. The method according to claim 1, wherein the CD47 blocking agent is administered to a subject that has undergone at least one course of the radiation treatment.

15. The method according to claim 1, wherein the subject has a tumour, and the CD47 blocking agent is injected or infused directly into the tumour.

16. The method according to claim 14, wherein the radiation treatment comprises a fractionation dosing schedule.

17. The method according to claim 1, wherein the CD47 blocking agent and the radiation treatment are given sequentially.

18. The method according to claim 1, further comprising administering or using a radiosensitizing drug during a course of the radiation treatment.

* * * * *